(12) United States Patent
Kumagai et al.

(10) Patent No.: US 12,290,602 B2
(45) Date of Patent: May 6, 2025

(54) CELLULOSE POWDER, USE THEREOF, AND TABLETS

(71) Applicant: ASAHI KASEI KABUSHIKI KAISHA, Tokyo (JP)

(72) Inventors: Tadahiro Kumagai, Tokyo (JP); Kaede Tamari, Tokyo (JP); Naoya Yoshida, Tokyo (JP)

(73) Assignee: ASAHI KASEI KABUSHIKI KAISHA, Tokyo (JP)

(*) Notice: Subject to any disclaimer, the term of this patent is extended or adjusted under 35 U.S.C. 154(b) by 822 days.

(21) Appl. No.: 17/415,403

(22) PCT Filed: Aug. 27, 2019

(86) PCT No.: PCT/JP2019/033506
§ 371 (c)(1),
(2) Date: Jun. 17, 2021

(87) PCT Pub. No.: WO2020/136995
PCT Pub. Date: Jul. 2, 2020

(65) Prior Publication Data
US 2022/0062182 A1  Mar. 3, 2022

(30) Foreign Application Priority Data

Dec. 27, 2018  (JP) .................... 2018-245362
Dec. 27, 2018  (JP) .................... 2018-245363

(51) Int. Cl.
  *A61K 9/20*  (2006.01)
  *A61K 31/433*  (2006.01)
  *A61K 31/496*  (2006.01)

(52) U.S. Cl.
  CPC .......... *A61K 9/2054* (2013.01); *A61K 9/2013* (2013.01); *A61K 9/2018* (2013.01); *A61K 9/2031* (2013.01); *A61K 31/433* (2013.01); *A61K 31/496* (2013.01)

(58) Field of Classification Search
  None
  See application file for complete search history.

(56) References Cited

U.S. PATENT DOCUMENTS

| | | |
|---|---|---|
| 2004/0043964 A1 | 3/2004 | Gomi et al. |
| 2004/0053887 A1 | 3/2004 | Obae et al. |
| 2005/0272836 A1 | 12/2005 | Yaginuma et al. |
| 2009/0022791 A1 | 1/2009 | Obae et al. |
| 2015/0110900 A1 | 4/2015 | Obae et al. |
| 2015/0150804 A1 | 6/2015 | Obae et al. |
| 2017/0258728 A1 | 9/2017 | Yoshida et al. |
| 2020/0146977 A1 | 5/2020 | Umemoto et al. |

FOREIGN PATENT DOCUMENTS

| | | | |
|---|---|---|---|
| CN | 1473054 A | 2/2004 | |
| EP | 1300420 A1 | 4/2003 | |
| EP | 1873196 A1 * | 1/2008 | .......... A23L 29/262 |
| EP | 2589618 A1 | 5/2013 | |
| EP | 3181616 A1 | 6/2017 | |
| JP | 2001-335469 A | 12/2001 | |
| JP | 2015-048315 A | 3/2015 | |
| JP | 2019-026558 A | 2/2019 | |
| JP | 2019-112358 A | 7/2019 | |
| TW | 1572360 B | 3/2017 | |
| WO | 02/002643 A1 | 1/2002 | |
| WO | 2006/115198 A1 | 11/2006 | |
| WO | 2013/180248 A1 | 12/2013 | |
| WO | 2013/180249 A1 | 12/2013 | |
| WO | WO-2013180246 A1 * | 12/2013 | ............. A61K 9/146 |
| WO | 2018/199282 A1 | 11/2018 | |

OTHER PUBLICATIONS https://www.3p-instruments.com/measurement-methods/density-tapping-volumetry/#:~: text=A%20tap%20starts%20with%20raising,higher%20than%20the%20bulk%20density. (Year: 2020).*
https://www.sssdynamics.com/resources/glossary-of-terms/#:~: text=Aerated%20Bulk%20Density%2C%20also%20known,subjected%20to%20compression%20or%20packing. (Year: 2013).*
Translated WO 2013/180246 A1 (Year: 2013).*
ISR issued in WIPO Patent Application No. PCT/JP2019/033506, Oct. 8, 2019. English translation.
Written Opinion issued in WIPO Patent Application No. PCT/JP2019/033506, Oct. 8, 2019. English translation.
European Search Report issued in EP Patent Application No. 19903077.6, Jan. 20, 2022.
Database WPI Week 201401, Dec. 5, 2013 (Dec. 5, 2013) Thomson Scientific, London, GB; AN 2013-W47791 XP002805256.

(Continued)

*Primary Examiner* — Andrew S Rosenthal
*Assistant Examiner* — Danielle Kim
(74) *Attorney, Agent, or Firm* — GREENBLUM & BERNSTEIN, P.L.C.

(57) ABSTRACT

The present invention provides a cellulose powder containing an alkali-soluble substance capable of dissolving in 17.5% by mass of aqueous sodium hydroxide solution, the content of the alkali-soluble substance being 32% by mass or more and 44% by mass or less with respect to the total mass of the cellulose powder, the use thereof, and tablets using the same.

14 Claims, No Drawings

(56) References Cited

OTHER PUBLICATIONS

Bowen P: "Particle Size Distribution Measurement from Millimeters to Nanometers and from Rods to Platelets", Journal of Dispersion Science and Technology, Taylor and Francis Group, New York, NY, US, vol. 23, No. 5, Jan. 1, 2002 (Jan. 1, 2002), pp. 631-662, XP009102859, ISSN: 0193-2691, DOI: 10.1081/DIS-120015368.
N.V. Lazarev, "Hazardous Substances in Industry." Handbook for chemists, engineers and doctors. 7th edition, vol. 3, Moscow, Chimia, 1977, translation.
T. Heinze et al., Celluloses and Polyoses/Hemicelluloses /Polymer Science: A Comprehensive Reference, 2012, vol. 10, pp. 84-152, p. 128 section 10.05.7.1.1.

* cited by examiner

CELLULOSE POWDER, USE THEREOF, AND TABLETS

TECHNICAL FIELD

The present invention relates to a cellulose powder, the use thereof, and tablets.

BACKGROUND ART

In preparations for oral administration such as tablets, the elution rate and elution time of active ingredients such as medicines are one of the important factors in the design of preparations. The elution rate of active ingredient is not unconditionally determined by the type of active ingredient, but determined by many factors such as the content of active ingredient, the dosage form, the formulation procedure, and the type and characteristics of pharmaceutical additive. Even when the same active ingredient is administered, since the difference in elution rate and elution time may cause a difference in manifestation of the medicine efficacy, it is necessary to control the elution rate and the elution time within a range suitable for each active ingredient. In particular, in so-called generic preparations, it is usually required to have an elution rate comparable to that of a new medicine to be compared. In addition, when formulating a poorly water-soluble medicinal ingredient, there are problems such as deterioration of disintegration property and decrease in dissolution rate.

On the other hand, in the elution test of active ingredient in vitro, in some cases, the elution is delayed due to the formation of mounts (sediments deposited in a mountain shape) on the bottom of the container, which makes it difficult to correctly evaluate the elution rate. It is considered that the elution is delayed because the flow rate of the solvent is small inside the mount and the active ingredient stays at a relatively high concentration inside the mount.

One of the causes of mounting is that the active ingredient and the water-insoluble pharmaceutical additives (excipient, etc.) form a physical aggregate and sink to the bottom. In order to suppress the formation of mounts, reducing the amount of pharmaceutical additives compounded or changing it to one with a lighter specific gravity can be one of the effective means. However, with regard to pharmaceutical products, it is often not possible to easily change the prescription (composition) once decided.

Crystalline cellulose is one of the typical pharmaceutical additives, but the true specific gravity of cellulose is about 1.5 times that of water, and it is a component that relatively easily sinks in water and easily forms a mount. However, since crystalline cellulose has excellent properties in terms of moldability, disintegration property, etc., if the blending amount of crystalline cellulose is reduced for the purpose of suppressing the generation of mounts, or if it is replaced with other components, it may affect other physical characteristics as a preparation. Therefore, it was not easy to improve the dissolution rate when mounts generated in the dissolution test of preparations using crystalline cellulose.

PTL 1 discloses a porous cellulose aggregate having a secondary aggregation structure in which primary cellulose particles are aggregated and having a pore volume in the particles in a specific range. It is described that the elution rate of a poorly water-soluble active ingredient can be improved by using the porous cellulose aggregate.

PTL 2 discloses a method for producing a preparation using a surfactant. It is described that the elution rate of poorly water-soluble medicinal ingredients can be improved by using a surfactant.

CITATION LIST

Patent Literature

[PTL 1] PCT International Publication No. WO 2006/115198

[PTL 2] Japanese Unexamined Patent Application, First Publication No. 2001-335469

SUMMARY OF INVENTION

Technical Problem

However, PTL 1 does not mention the generation of mounts during the elution test of active ingredient in vitro.

Further, since the addition of a solubilizer such as a surfactant causes a decrease in the hardness and moldability of the tablet, it is required to reduce the amount of solubilizer used.

The present invention has been made in view of the above circumstances, and provides a cellulose powder capable of suppressing generation of mounts during the elution test of active ingredient in vitro while maintaining good moldability and disintegration properties, and also provides a method for suppressing generation of mount using the cellulose powder.

The present invention also provides a tablet containing a poorly water-soluble medicinal ingredient and having good moldability, disintegration property and dissolution property.

Solution to Problem

As a result of intensive studies to achieve the above object, the present inventors have found that cellulose powder containing an alkali-soluble substance within a specific range can suppress generation of mounts during the elution test of active ingredient in vitro, and can improve disintegration and elution properties while maintaining good moldability of tablets containing a poorly water-soluble medicinal ingredient. Based on these findings, the present inventors have accomplished the present invention.

That is, the present invention includes the following aspects.

[1] A cellulose powder comprising an alkali-soluble substance capable of dissolving in 17.5% by mass of aqueous sodium hydroxide solution, the content of the alkali-soluble substance being 32% by mass or more and 44% by mass or less with respect to the total mass of the cellulose powder.

[2] The cellulose powder according to [1], wherein the alkali-soluble substance is contained in an amount of 33% by mass or more and 42% by mass or less with respect to the total mass of the cellulose powder.

[3] The cellulose powder according to [1], wherein the average particle size of primary particles of the cellulose powder is 10 μm or more and 50 μm or less.

[4] The cellulose powder according to [1] or [2], wherein the water absorption amount is 160% or more and 360% or less.

[5] The cellulose powder according to any one of [1] to [3], wherein the ratio (L/D) of the major axis to the minor axis of the cellulose particles is 1.8 or more and 3.5 or less.

[6] The cellulose powder according to any one of [1] to [5], wherein the average particle size is 10 μm or more and 200 μm or less.
[7] A method for suppressing mount formation, wherein the cellulose powder defined in any one of [1] to [4] is used for a preparation to be subjected to a dissolution test of active ingredient.
[8] A tablet comprising at least one active ingredient, and the cellulose defined in any one of [1] to [7].
[9] The tablet according to [8], wherein the active ingredient is a poorly water-soluble medicinal ingredient.
[10] The tablet according to [9], wherein the medicinal ingredient is classified as Class 2 or Class 4 according to the regulations of the biopharmaceutical classification system adopted by the FDA.
[11] The tablet according to any one of [8] to [10], further comprising a solubilizer in an amount of 0.1% by mass or more and 30% by mass or less with respect to the total mass of the tablet.
[12] The tablet according to any one of [8] to [11], wherein hardness of the tablet is 50 N or more.
[13] The tablet according to any one of [8] to [12], wherein the content of the cellulose is 1% by mass or more and 99% by mass or less with respect to the total mass of the tablet.
[14] The tablet according to any one of [8] to [13], wherein the content of the medicinal ingredient is 0.01% by mass or more and 50% by mass or less with respect to the total mass of the tablet.

Advantageous Effects of Invention

According to the cellulose powder of the above aspect, it is possible to provide a cellulose powder capable of suppressing generation of mounts during the elution test of active ingredient in vitro while maintaining good moldability and disintegration property. According to the method of the above aspect, it is possible to suppress generation of mounts during the dissolution test of active ingredient in vitro.

In addition, the tablet of the above aspect contains a poorly water-soluble medicinal ingredient and has good moldability, disintegration property and elution property.

DESCRIPTION OF EMBODIMENTS

Hereinafter, embodiments for carrying out the present invention (hereinafter, simply referred to as "the present embodiment") will be described in detail. The present invention is not limited to the following embodiments, and can be variously modified and implemented within the scope of the gist thereof.
<Cellulose Powder>
Cellulose powder is generally referred to as crystalline cellulose, powdered cellulose or the like, and is suitably used as a pharmaceutical additive or a food additive. Crystalline cellulose is preferable as the cellulose powder. Examples of the crystalline cellulose include microcrystalline cellulose described in the 8th edition of the Food Additives Official Regulations, crystalline cellulose described in the Japanese Pharmacopoeia (17th revision), crystalline celluloses described in the United States Pharmacopeia, the European Pharmacopoeia and the like.

The cellulose powder of the present embodiment preferably has an average particle size of 10 μm or more and 200 μm or less, more preferably 15 μm or more and 150 μm or less, even more preferably 18 μm or more and 130 μm or less, particularly preferably 20 μm or more and 120 μm or less, and most preferably 20 μm or more and 100 μm or less.

When the average particle size is within the above range, it is possible to effectively suppress the generation of mounts during the elution test of the active ingredient in vitro, and at the same time, improve the compression moldability and the disintegration property. In particular, when the average particle size is 20 μm or more, the fluidity of the powder is improved.

The average particle size of the cellulose powder is a particle size at a cumulative volume of 50% measured by a laser diffraction type particle size distribution meter (trade name: LA-950 V2, manufactured by HORIBA, Ltd.).

It can be considered that when the cellulose powder of the present embodiment contains an alkali-soluble substance capable of dissolving in a 17.5% by mass aqueous solution of sodium hydroxide, it easily absorbs water moderately, attracts water into the cellulose particles, and easily flows up in the water stream. Therefore, by using the cellulose powder of the present embodiment, it is possible to suppress the generation of mounts (precipitation) during the elution test of active ingredient in vitro. The "elution test of active ingredient in vitro" as used herein, specifically refers to a test for eluting one tablet under the conditions of 900 mL of water, 37° C., and a paddle rotation speed of 50 rpm, as described in Examples later.

In addition, the tablet containing the cellulose powder of the present embodiment can accelerate the disintegration of the tablet in vivo, and the release of active ingredient is good. Therefore, the cellulose powder of the present embodiment is suitable for an orally disintegrating tablet (OD tablet).

The lower limit of the content of the alkali-soluble substance in the cellulose powder of the present embodiment is 32% by mass, preferably 33% by mass, and more preferably 34% by mass, with respect to the total mass of the cellulose powder. On the other hand, the upper limit of the content of the alkali-soluble substance is 44% by mass, preferably 42% by mass, more preferably 41% by mass, with respect to the total mass of the cellulose powder.

That is, the content of the alkali-soluble substance in the cellulose powder is 32% by mass or more and 44% by mass or less, preferably 33% by mass or more and 42% by mass or less, and more preferably 34% by mass or more and 41% by mass or less, with respect to the total mass of the cellulose powder.

When the content of the alkali-soluble substance in the cellulose powder of the present embodiment is within the above range, the generation of mounts can be effectively suppressed.

Further, when used for an orally disintegrating tablet, the content of the alkali-soluble component is preferably 32% by mass or more with respect to the total mass of the cellulose powder because it has excellent disintegrating property in the oral cavity.

The alkali-soluble substance capable of dissolving in a 17.5% by mass of aqueous sodium hydroxide solution in the cellulose powder can be measured by the following method.

Specifically, first, 1 g of each cellulose powder is weighed in a 50-mL plastic centrifuge tube (here, the weight of the actually weighed cellulose powder is defined as M1 [g]). 25 mL of a 17.5 mass % sodium hydroxide aqueous solution is added at room temperature (20° C.), the aqueous solution is stirred with a spatula, and the entire cellulose powder is immersed in the sodium hydroxide aqueous solution and allowed to stand. After 30 minutes have passed from the addition of the sodium hydroxide aqueous solution, 10 mL of distilled water is added, stirred with a spatula, and allowed to stand for 5 minutes. Next, the aqueous solution is centrifuged (centrifugal force: 15000 G, time: 20 minutes, temperature: 20° C.) to precipitate the solid content, and 20 mL of the supernatant is sucked up with a dropper and discarded. 25 mL of distilled water is added to the remaining precipitate and solution and stirred with a spatula. Then, the aqueous solution is centrifuged (15000 G×20 minutes) to precipitate the solid content, and 25 mL of the supernatant is discarded. After performing the above washing operation twice more, 25 mL of a 10 mass % acetic acid aqueous solution is added and stirred with a spatula to adjust the liquid property to acidic. Next, the prepared solution is suction-filtered with a 1G3 glass filter whose mass (T1 [g]) at the time of drying has been measured in advance. The solid matter remaining on the glass filter is washed with 40 mL of a 10 mass % acetic acid aqueous solution, and then washed with 500 mL of boiling water (98° C.). The washed powder (solid matter) is placed in an oven at 105° C. together with the glass filter and dried for 6 hours or more. The powder and the glass filter are taken out from the oven, placed in a desiccator containing silica gel as a desiccant, cooled to room temperature, and the mass (W1 [g]) is measured. Further, in the above test, a blank test is performed using distilled water instead of the 17.5 mass % sodium hydroxide aqueous solution. In the blank test, the weight of the cellulose actually weighed is defined as MB [g], the mass of the glass filter is defined as TB [g], and the mass of the powder is defined as WB [g].

Using the obtained M1, T1, W1, MB, TB and WB, the content (%) of the alkali-soluble substance can be calculated by the formula shown below.

$$\text{Alkali-soluble substance content (\%)} = \{(W1-T1)\,[g]/M1\,[g] - (WB-TB)\,[g]/MB\,[g]\} \times 100$$

The content of the alkali-soluble substance in the cellulose powder can be adjusted, for example, by appropriately changing the conditions for hydrolysis of the cellulose. Specifically, for example, the content of the alkali-soluble substance in the cellulose powder can be increased by a method of increasing the concentration of the acid used for hydrolysis, a method of increasing the shearing force acting on the cellulose, a method of increasing the hydrolysis treatment time, or the like.

Further, for example, by physically crushing the cellulose powder into small particles, the content of the alkali-soluble substance in the cellulose powder tends to increase. Further, for example, the content of the alkali-soluble substance in the cellulose powder can be adjusted by a method of mixing two or more kinds of aqueous cellulose dispersions produced under different conditions and drying them.

The cellulose powder of the present embodiment preferably has an aerated bulk density of 0.10 g/cc or more and 0.34 g/cc or less, more preferably 0.11 g/cc or more and 0.33 g/cc or less, even more preferably 0.12 g/cc or more and 0.30 g/cc or less, and particularly preferably 0.13 g/cc or more 0.24 g/cc. When the aerated bulk density is within the above range, the compression moldability can be further improved while effectively suppressing the generation of mounts during the elution test of active ingredient in vitro.

The aerated bulk density can be measured by using the method described in Examples later.

The cellulose powder of the present embodiment preferably has a packed bulk density of 0.25 g/cc or more and 0.60 g/cc or less, more preferably 0.26 g/cc or more and 0.58 g/cc or less, and even more preferably 0.28 g/cc or more and 0.57 g/cc or less. When the packed bulk density is at least the above lower limit, it is easily and uniformly mixed with the active ingredient such as a drug, and the handleability can be improved. On the other hand, when the packed bulk density is not more than the above upper limit, segregation of the active ingredient can be effectively suppressed.

The packed bulk density can be measured using the method described in Examples later.

The cellulose powder of the present embodiment preferably has a compression ratio of 21% or more and 70% or less, more preferably 23% or more and 60% or less, even more preferably 25% or more and 48% or less, and particularly preferably 25% or more and 44% or less. When the compression ratio is within the above range, fluidity of the cellulose powder itself is good, which is preferable from the viewpoint of suppressing segregation.

The compression ratio can be calculated using the method described in Examples later.

In the cellulose powder of the present embodiment, the whiteness is preferably 80 or more and 100 or less, more preferably 90 or more and 100 or less, and even more preferably 95 or more and 100 or less. When the whiteness is within the above range, the obtained tablet is white and has excellent aesthetic appearance.

The whiteness can be measured using the method described in Examples later.

In the cellulose powder of the present embodiment, the water absorption amount is preferably 160% or more and 360% or less, and more preferably 160% or more and 350% or less. The "water absorption amount" as used herein is an index of how much water the cellulose powder absorbs based on the weight of the cellulose powder. When the water absorption amount is within the above range, the generation of mounts (precipitation) during the elution test of active ingredient in vitro can be more effectively suppressed, and the disintegration property when made into a tablet can be improved.

The amount of water absorption can be calculated using the method shown below. First, 2 g of the cellulose powder is weighted in a 50-mL plastic centrifuge tube (the mass actually weighed is defined as "Wi" [g]), 30 mL of pure water is added, and the resulting mixture is dispersed while stirring with a spatula, so as to entirely immerse the cellulose powder in the pure water. After standing the resulting mixture for 30 minutes, the solid content is precipitated by centrifugation (centrifugal force: 7500 G, time: 10 minutes, temperature: 20° C.). The opening of the centrifuge tube is tilted downward so as not to break the precipitated cellulose layer, thereby removing the supernatant, and the opening of the centrifuge tube is tilted downward by 30° from the horizontal and allowed to stand for 5 minutes on a table laid with a paper towel to drain the excess water. Next, the mass (Wf [g]) of the water-absorbed cellulose powder is measured.

Using the obtained Wi and Wf, the water absorption amount (%) can be calculated by the formula shown below.

$$\text{Water absorption amount (\%)} = (Wf - Wi)/Wi \times 100$$

In the cellulose powder of the present embodiment, the average particle size of the primary particles is preferably 10 μm or more and 50 μm or less, and more preferably 15 μm or more and 30 μm or less. When the particle size of the primary particles is within the above range, they are easily and uniformly mixed with the active ingredient such as drugs, and the disintegration property when made into a tablet is improved.

The primary particles are unit particles, and those in which the primary particles are aggregated are called secondary particles (aggregate, agglomerate). When the secondary particles are dispersed in water, the agglutination is released and the secondary particles can be returned to primary particles. The average particle size of the primary particles can be measured using the method described in Examples later.

In the cellulose powder of the present embodiment, the ratio of the major axis to the minor axis of the cellulose particles, that is, the aspect ratio (L/D) is preferably 1.8 or more and 4.0 or less, more preferably 2.0 or more and 3.8 or less, and even more preferably 2.2 or more and 3.5 or less. When the aspect ratio is within the above range, the mixability with active ingredient is good, and the balance between moldability and disintegration property is excellent.

The aspect ratio (L/D) can be measured using the method described in Examples later.

In the cellulose powder of the present embodiment, the lower limit of the repose angle is preferably 34°, more preferably 36°, even more preferably 37°, and particularly preferably 43°. When the repose angle is equal to or higher than the above lower limit, the powder tends to flow up in the water stream, and it becomes difficult to form mounts.

On the other hand, although the upper limit of the repose angle is not particularly limited, it is theoretically less than 90°. The repose angle is an index of fluidity generally used in the field of powders, and the lower the repose angle, the better the fluidity, and it becomes easier to mix uniformly with medicinal ingredients and other ingredients. From the viewpoint of a balance between the formation of mounts and the fluidity, the upper limit of repose angle is preferably 80°, more preferably 70°, and even more preferably 60°.

<Manufacturing Method of Cellulose Powder>

The method for producing the cellulose powder of the present embodiment will be described below.

The cellulose powder of the present embodiment can be obtained, for example, by a method including a step of obtaining a cellulose aqueous dispersion by dispersing a hydrolyzed natural cellulose substance in an appropriate medium and a step of drying the aqueous dispersion. The solid content concentration of the aqueous cellulose dispersion is not particularly limited, and can be, for example, 1% by mass or more and 30% by mass or less. In this case, the solid content containing the hydrolyzed cellulose substance may be isolated from the hydrolysis reaction solution obtained by hydrolysis treatment, then dispersed in an appropriate medium to prepare a dispersion, followed by drying the dispersion. Alternatively, the hydrolysis solution may be dried directly.

The natural cellulose substance may be of vegetable or animal origin, and it is preferably a fibrous substance derived from a natural substance containing cellulose such as wood, bamboo, cotton, ramie, sea squirt, bagasse, kenaf, bacterial cellulose or the like and having an I-type crystal structure. As the raw material, one of the above natural cellulose substances may be used, or a mixture of two or more of them may be used. Further, it is preferably used in the form of refined pulp, but the method for refining the pulp is not particularly limited, and any pulp such as dissolved pulp, kraft pulp, and NBKP pulp may be used.

In the above-mentioned production method, water is preferable as the medium used when the solid content containing the natural cellulose substance is dispersed in an appropriate medium, but there is no particular limitation as long as it is used industrially, and for example, an organic solvent may also be used. Examples of the organic solvent include alcohols such as methanol, ethanol, isopropyl alcohol, butyl alcohol, 2-methylbutyl alcohol, benzyl alcohol or the like; hydrocarbons such as pentane, hexane, heptane, cyclohexane or the like; and ketones such as acetone, ethyl methyl ketone or the lie. In particular, the organic solvent is preferably a solvent used in pharmaceutical products, and examples thereof include the solvents classified as a solvent in the "Encyclopedia of Pharmaceutical Additives" (published by Yakuji Nippo, LTD.). Water and the organic solvents may be used alone or in combination of two or more, or the solid content may be dispersed once in one medium, then dispersed in a different medium after removing the medium.

The average particle size of the cellulose particles (dispersed cellulose particles) in the aqueous dispersion is preferably 10 μm or more and 200 μm or less, more preferably 15 μm or more and 100 μm or less, and particularly preferably 15 μm or more and 50 μm or less. When the average particle size in the dispersion is within the above range, it is easy to obtain cellulose particles having an average particle size of 10 μm or more and 200 μm or less after drying.

The average particle size of dispersed cellulose particles can be controlled within a desired range by adjusting the degree of polymerization of the raw material cellulose by hydrolysis, and adjusting the stirring force of at least one of the cellulose hydrolysis and dispersion steps. In general, when the acid concentration, alkali concentration and reaction temperature of the hydrolyzed solution are increased, the degree of polymerization of cellulose tends to decrease, the average particle size of the cellulose in the dispersion tends to decrease, and even if the stirring force of the solution is strengthened, the average particle size of the dispersed cellulose particles tends to decrease.

Although acids or alkalis can be used to hydrolyze natural cellulose substances, acids are often used industrially. The acid concentration at the time of hydrolysis is preferably 0.01% by mass or more and 1.0% by mass or less. When the acid concentration is within the above range, the average particle size of the dispersed cellulose particles can be easily controlled in a range of 10 μm or more and 200 μm or less, and the content of the alkali-soluble substance can be easily controlled in a range of 32% by mass or more and 44% by mass or less.

For example, pulp fibers having an average width of 2 μm or more and 30 μm or less and an average thickness of 0.5 μm or more and 5 μm or less are hydrolyzed in a hydrochloric acid of 0.01% by mass or more and 1.0% by mass or less at a temperature of 70° C. or higher and 140° C. or lower under pressure while rotating a stirrer.

The progress of hydrolysis can be controlled by adjusting the motor power (P: unit W) and stirring capacity (L: unit L) of the stirrer. For example, by adjusting the P/V represented by the following formula, the average particle size of the finally obtained cellulose particles can be controlled to 200 μm or less, and the content of the alkali-soluble substance can be kept within a specific range.

$$P/V(W/L) = [\text{actual motor power of stirrer } (W)]/[\text{stirring capacity } (L)]$$

The drying method for drying the cellulose aqueous dispersion to obtain the cellulose powder is not particularly limited. For example, any of freeze-drying, spray-drying, drum-drying, shelf-drying, air-flow drying, and vacuum-drying may be used. These methods may be used alone, or in combination of two or more. The spraying method for spray-drying may be any of a disc type, pressurized nozzle, pressurized two-fluid nozzle, pressurized four-fluid nozzle, or the like. These methods may be used alone, or in combination of two or more.

At the time of spray-drying, a trace amount of water-soluble polymer and surfactant may be added for the purpose of lowering the surface tension of the dispersion liquid, and a foaming agent or gas may be added to the dispersion liquid for the purpose of accelerating the vaporization rate of the medium.

By controlling the acid concentration and stirring conditions when preparing the aqueous cellulose dispersion, a cellulose aqueous dispersion containing dispersed cellulose particles having an average particle size of a specific size and an alkali-soluble substance content within a specific range can be obtained, and further, by adjusting the solid content concentration of the cellulose aqueous dispersion and drying conditions when drying the cellulose aqueous dispersion, the average particle size, compression ratio, and repose angle of the obtained cellulose powder can be controlled. For example, when the cellulose aqueous dispersion is dried by a disc type spray-drying, by setting the stirring force to a specific range during the preparation of the cellulose aqueous dispersion and setting the solid content concentration of the cellulose aqueous dispersion and the rotation speed of the disc type spray-drying within a specific range during the spray-drying, a cellulose powder having specific ranges of average particle size, alkali-soluble substance content, compression ratio and repose angle can be obtained.

Further, as described in the Examples later, by mixing two or more kinds of aqueous cellulose dispersions and drying, a cellulose powder having specific ranges of average particle size and alkali-soluble substance content may be obtained.

Even when the average particle size of the dried cellulose powder is larger than 200 μm, the average particle size can be adjusted to 10 μm or more and 200 μm or less by subjecting it to a pulverization step described later.

In the pulverization step, the dried cellulose powder can be pulverized with pulverizers such as an ultracentrifugal pulverizer (ZM-200, manufactured by Resch), a jet mill (STJ-200, manufactured by Seishin Enterprise Co., Ltd.), a hammer mill (H-12, manufactured by Hosokawa Micron), a bantam mill (AP-B, manufactured by Hosokawa Micron), a pin mill (160Z, manufactured by Paulek), Fezamil (FM, manufactured by Hosokawa Micron), a hammer mill (HM-600, manufactured by Nara Machinery Co., Ltd.), a flash mill (FL-250N, manufactured by Dalton), a ball mill (Emax, manufactured by Resch), a vibrating ball mill (2C, manufactured by TRU), a screen mill passing through the screen (U30, manufactured by Paulec). In particular, a jet mill pulverizer (STJ-200, manufactured by Seishin Enterprise Co., Ltd.) is preferable because it is a flow-type pulverizer that pulverizes particles while colliding the particles with a high air pressure, and the secondary particles are easily pulverized into the primary particles.

As for the pulverizing conditions of the jet mill pulverizer, the powder supply amount and the pulverizing pressure are important, and when the jet mill pulverizer (STJ-200, manufactured by Seishin Enterprise Co., Ltd.) is used, the supply amount is preferably 10 kg/hour or more and 20 kg/hour or less, and more preferably 15 kg/hour or more and 20 kg/hour or less. The pulverizing pressure is preferably 0.15 MPa or more and 0.70 MPa or less, and more preferably 0.30 MPa or more and 0.50 MPa or less. When the powder supply amount and the pulverizing pressure are within the above ranges, the average particle size tends to be easily controlled to 15 μm or more and 200 μm or less.

<Usage>

By blending the cellulose powder of the embodiment with a composition containing an active ingredient, it is possible to obtain a tablet in which generation of mounts is suppressed during the dissolution test of active ingredient in vitro while maintaining good moldability and disintegration properties. The cellulose powder of this embodiment is suitable for orally disintegrating tablets (OD tablet).

<Tablet>

The tablet of the present embodiment contains a poorly water-soluble medicinal ingredient and the cellulose powder of the present embodiment.

By having the above-mentioned configuration, the tablet of the present embodiment can have good moldability, disintegration property and elution property even if it contains a poorly water-soluble medicinal ingredient.

The components of the tablet of the present embodiment will be described in detail below.

[Cellulose Powder Content]

Although the mixing ratio of the cellulose powder to the tablet of the present embodiment can be any ratio, 90% by mass or less with respect to the total mass of the tablet is a practically preferable range. The lower limit is practically 0.1% by mass. When used in tablets containing a large amount of active ingredient, it is preferably about 0.1% by mass or more and 50% by mass or less, more preferably 0.1% by mass or more and 20% by mass or less, and even more preferably 0.1% by mass or more and 10% by mass or less.

Further, when the tablet of the present embodiment contains a poorly water-soluble medicinal ingredient described later, the content of cellulose is preferably 1% by mass or more and 99% by mass or less, more preferably 10% by mass or more and 90% by mass or less, even more preferably 15% by mass or more and 80% by mass or less, and particularly preferably 15% by mass or more and 50% by mass or less with respect to the total mass of the tablet.

When the content of cellulose is within the above range, moldability, disintegration property and dissolution property of the tablet can be improved.

[Water-Insoluble Medicinal Ingredient]

As used herein, the term "poorly water-soluble" means that the amount of water required to dissolve 1 g of a solute is 30 mL or more as defined in the 17th revised Japanese Pharmacopoeia.

The poorly water-soluble medicinal ingredient contained in the tablet of the present embodiment is not particularly limited, but is preferably classified as Class 2 (low solubility, good membrane permeability) or Class 4 (low solubility, poor membrane permeability) in the regulations of the Biopharmaceutical Classification System adopted by the FDA.

Specifically, as those classified as Class 2, for example, artesunate, azithromycin, carbamazepine, cefixime, diaphenyl sulfone, etoposide, griseofulvin, ibuprofen, iopanoic acid, itraconazole, lopinavir, mebendazole, mefloquine hydrochloride, mercaptopurine, nevirapine, nifedipine, nitrofurantoin, oxamniquine, 4-aminosalicylic acid, sodium phenytoinate, praziquantel, rifampicin, sulfamethoxazole, trimethoprim, verapamil hydrochloride or the like can be mentioned.

Specifically, as those classified as Class 4, for example, acetazolamide, albendazole, artemether, artesunate, azathioprine sodium salt, azithromycin, cefixime, clofazimine, cyclosporine, diloxanide furoate, efavirenz, etoposide, furosemide, glibenclamide, haloperidol, indinavir sulfate, ivermectin, lopinavir, lumefantrine, mebendazole, mefloquine hydrochloride, mercaptopurine, mifepristone, misoprostol, nelfinavir mesylate, niclosamide, oxamniquine, 4-aminosalicylic acid, pyrantel pamoate, pyrimethamine, retinol palmitate, ritonavir, saquinavir, spironolactone, sulfadiazine, salazosulfapyridine, triclabendazole or the like can be mentioned.

These poorly water-soluble medicinal ingredients may be blended in the tablet of the present embodiment in a finely pulverized state together with the above-mentioned cellulose. For example, the poorly water-soluble medicinal ingredient used in the present specification is used for the purpose of improving the dispersibility of the poorly water-soluble medicinal ingredient, or improving the mixing uniformity of the poorly water-soluble medical ingredient having medicinal effects and contained in a small amount. The average particle size is preferably 1 µm or more and 40 µm or less, more preferably 1 µm or more and 20 µm or less, and even more preferably 1 µm or more and 10 µm or less.

The content of the poorly water-soluble medicinal component in the tablet of the present embodiment is preferably 0.01% by mass or more and 50% by mass or less, more preferably 0.05% by mass or more and 49% by mass or less, even more preferably 0.1% by mass or more and 48% by mass or less, and particularly preferably 1% by mass or more and 45% by mass or less, with respect to the total mass of the tablet.

[Solubilizer]

In addition to the above-mentioned cellulose and the above-mentioned poorly water-soluble medicinal ingredient, the tablet of the present embodiment may contain a solubilizer as a component that assists the dissolution of the poorly water-soluble medicinal ingredient.

As the solubilizer, those described in "Pharmaceutical Additives Dictionary" (published by Published by Yakuji Nippo, LTD.) can be appropriately used, and examples thereof include surfactants such as a polyalkylene glycol, blocked copolymer type polyalkylene glycol, polyoxyethylene alkyl ether phosphate, polyethylene glycol fatty acid ester, polyoxyethylene hydrogenated castor oil, polyoxyethylene sorbitan fatty acid ester, polyoxyethylene glycerin fatty acid ester, polyoxyethylene alkyl ether, polyoxyethylene alkyl allyl ether or the like.

Examples of the polyalkylene glycol include polyethylene glycol (PEG) and the like. Examples of commercially available PEG products used for pharmaceutical products include Macrogol 4000, Macrogol 6000 and the like.

Examples of the blocked copolymer type polyalkylene glycol include polyoxyethylene (160) polyoxypropylene (30) glycol and the like.

Examples of the polyoxyethylene alkyl ether phosphate include polyoxyethylene cetyl ether sodium phosphate and the like.

Examples of the polyethylene glycol fatty acid ester include polyethylene glycol monooleate, polyethylene glycol dioleate and the like.

Examples of the polyoxyethylene sorbitan fatty acid ester include polyoxyethylene (20) sorbitan monooleate (polysorbate 80) and the like.

Examples of the polyoxyethylene glycerin fatty acid ester include polyoxyethylene glycerin monostearate and the like.

Examples of the polyoxyethylene alkyl ether include polyoxyethylene lauryl ether and the like.

Examples of the polyoxyethylene alkyl allyl ether include polyoxyethylene nonylphenyl ether and the like.

The content of the solubilizer in the tablet of the present embodiment is preferably 0.1% by mass or more and 30% by mass or less with respect to the total mass of the tablet.

In the tablet of the present embodiment, by containing the above-mentioned cellulose, it is possible to obtain a tablet having excellent moldability, disintegration property and elution property while having the above-described range of the solubilizer content.

[Other Active Ingredients]

In the present specification, the active ingredient refers to an ingredient added to a mixed powder, a molded product, a processed product, or the like in order to exert a desired function or effect in the fields of pharmaceutical products, health food, food products, industry and the like. For example, an active ingredient in the pharmaceutical field is a medicinal ingredient of pharmaceutical products.

Hereinafter, suitable active ingredients contained in the tablet of the present embodiment will be listed.

As the medicinal ingredient of a pharmaceutical product, an active ingredient of an orally administered pharmaceutical product is preferable. Examples of the orally administered pharmaceutical product include anti-pyretic an analgesic anti-inflammatory drug, hypnotic sedative, anti-drowsiness drug, anti-spasmodic, pediatric analgesics, stomach medicine, antacid, digestive, cardiotonic drug, arrhythmia drug, anti-hypertensive drug, vasodilator, diuretic, anti-ulcer drug, intestinal medicine, osteoporosis remedy, anti-tussive expectorant, anti-asthma drug, anti-bacterial agent, frequent urination improver, nourishing tonic, vitamin preparations and the like. The medicinal ingredients may be used alone or in combination of two or more.

Specifically, examples of the medicinal ingredient include the medicinal ingredients of pharmaceutical products listed in "Japanese Pharmacopoeia", "The Japanese Pharmaceutical Codex (JPC)", "the United States Pharmacopeia (USP)", "the National Formulary (NF)" and "European Pharmacopoeia (EP)", such as aspirin, aspirin aluminum, acetaminophen, ethenzamide, sazapyrin, salicylamide, lactyl phenetidine, isotibenzyl hydrochloride, diphenylpyraline hydrochloride, diphenhydramine hydrochloride, dipherol hydrochloride, riprolidine hydrochloride, tryperenamine hydrochloride, tonzilamine hydrochloride, fenetazine hydrochloride, metodirazine hydrochloride, diphenhydramine salicylate, carbinoxamine diphenyldisulfonate, alimemazine tartrate, diphenhydramine tannate, diphenylpyraline theocrate, mebhydrolin napadisylate, promethazine methylene disalicylate, carbinoxamine maleate, dl-chlorpheniramine maleate, d-chlorpheniramine maleate, dipherol phosphate, alloclamide hydrochloride, cloperastin hydrochloride, pentoxiberin citrate (carbetapentane citrate), tipepidine citrate, sodium dibunato, dextromethorphan hydrobromide, dextromethorphan phenolphthalic acid, tipepidine hibenzate, cloperastin fendyzoate, codeine phosphate, dihydrocodeine phosphate, noscapine hydrochloride, noscapine, dl-methylephedrine hydrochloride, dl-methylephedrine saccharin salt, potassium guaiacol sulfonate, guaifenesin, sodium benzoate caffeine, caffeine, anhydrous caffeine, vitamin B1 and its derivatives and their salts, vitamin B2 and its derivatives and their salts, vitamin C and its derivatives and their salts, hesperidin and its derivatives and their salts, vitamin B6 and its derivatives and their salts, nicotinamide, calcium pantothenate, amino acetate, magnesium silicate, synthetic aluminum silicate, synthetic hydrotalcite, magnesium oxide, dihydroxyaluminum aminoacetate (aluminum glycinate), aluminum hydroxide gel (as dry aluminum hydroxide gel), dry aluminum hydroxide gel, aluminum hydroxide/magnesium carbonate mixed dry gel, aluminum hydroxide/sodium hydrogen carbonate coprecipitation product, aluminum hydroxide/calcium carbonate/ magnesium carbonate coprecipitation product, magnesium hydroxide/potassium aluminum sulfate coprecipitation product, magnesium carbonate, magnesium aluminate metasilicate, ranitidine hydrochloride, cimetidine, famotidine, naproxen, diclophenac sodium, piroxicam, azulene, indomethacin, ketoprofen, ibuprofen, diphenidol hydrochloride, diphenylpyraline hydrochloride, diphenhydramine hydrochloride, promethazine hydrochloride, meclizine Hydrochloride, dimenhydrinate, diphenhydramine tannate, fenetazine tannate, diphenylpyraline theocrate, diphenhydramine fumarate, promethazine methylene disalicylate, spocolamine hydrobromide, oxyphencyclimine hydrochloride, dicycloverine hydrochloride, metixene hydrochloride, methylatropine bromide, methylanisotropin bromide, methylspocolamine bromide, methyl-1-hyoscyamine bromide, methyl benactidium bromide, belladonna extract, isopropamide iodide, diphenylpiperidinomethyldioxolane iodide, papaverine hydrochloride, aminobenzoic acid, cesium oxalate, ethyl piperidylacetylaminobenzoate, aminophylline, diprophylline, theophylline, sodium bicarbonate, fursultiamine, isosorbide nitrate, ephedrine, cephalexin, ampicillin, sulfixazole, sucralfate, allyl isopropyl acetyl urea, bromvalerylurea or the like, ephedra, nandina fruit, cherry tree bark, polygala root, licorice, *Platycodon grandiflorum*, plantago seed, senega, fritillaria bulb, fennel, phellodendron bark, coptis rhizome, curcuma rhizome, chamomile, cinnamon, gentiana, oriental bezoar, beast gall (including bear's gall), ladybells, ginger, *Atractylodes lancea* rhizome, clove, citrus unshiu peel, atractylodes rhizome, earthworm, panax rhizome, ginseng, valerian, moutan bark, Japanese zanthoxylum peel and extracts thereof, insulin, vasopressin, interferon, urokinase, serratiopeptidase, somatostatin and the like. These ingredients may be used alone, or in combination of two or more.

The active ingredient of health food is not limited as long as it is an ingredient blended for the purpose of enhancing health, and examples thereof include powdered green juice, aglycone, agaricus, ashwagandha, astaxanthin, acerola, amino acids (valine, leucine, isoleucine, lysine, methionine, phenylalanine, threonine, tryptophan, histidine, cystine, tyrosine, arginine, alanine, aspartic acid, powdered seaweed, glutamine, glutamic acid, glycine, proline, serine, etc.), alginic acid, *Ginkgo biloba* extract, sardine peptides, turmeric, uronic acid, echinacea, *Siberian ginseng*, oligosaccharides, oleic acid, nucleoproteins, dried skipjack peptides, catechin, potassium, calcium, carotenoid, garcinia cambogia, L-carnitine, chitosan, conjugated linoleic acid, *Aloe arborescens*, *Gymnema sylvestre* extract, citric acid, *Orthosiphon stamineus*, glycerides, glycenol, glucagon, curcumin, glucosamine, L-glutamine, chlorella, cranberry extract, *Uncaria tomentosa*, germanium, enzymes, Korean ginseng extract, coenzyme Q10, collagen, collagen peptides, *Coleus blumei*, chondroitin, powdered psyllium husks, Crataegi fructus extract, saponin, lipids, L-cystine, Japanese basil extract, citrimax, fatty acids, phytosterol, seed extract, spirulina, squalene, *Salix alba*, ceramide, selenium, St. John's wort extract, soy isoflavone, soy saponin, soy peptides, soy lecithin, monosaccharides, proteins, chaste tree extract, iron, copper, docosahexaenoic acid, tocotrienol, nattokinase, Bacillus natto culture extract, sodium niacin, nicotine acid, disaccharides, lactic acid bacterium, garlic, saw palmetto, sprouted rice, pearl barley extract, herb extract, valerian extract, pantothenic acid, hyaluronic acid, biotin, chromium picolinate, vitamin A, vitamin A2, vitamin B1, vitamin B2, vitamin B6, vitamin B12, vitamin C, vitamin D, vitamin E, vitamin K, hydroxytyrosol, bifidobacterium, beer yeast, fructo oligosaccharides, flavonoid, Butcher's broom extract, black cohosh, blueberry, prune concentrate, proanthocyanidin, proteins, propolis, bromelain, probiotics, phosphatidylcholine, phosphatidylserine, β-carotene, peptides, safflower extract, *Grifola frondosa* extract, maca extract, magnesium, milk thistle, manganese, mitochondria, mineral, mucopolysaccharides, melatonin, Fomes yucatensis, powdered melilot extract, molybdenum, vegetable powder, folic acid, lactose, lycopene, linolic acid, lipoic acid, phosphorus, lutein, lecithin, rosmarinic acid, royal jelly, DHA, EPA and the like.

The active ingredient may be poorly-soluble or soluble in water. The term "poorly-soluble" refers to 30 mL or more of water being required to dissolve 1 g of a solute in the Japanese Pharmacopoeia Seventeenth Edition.

Examples of the solid active ingredient poorly-soluble in water include the medicinal ingredients of pharmaceutical product described in "Japanese Pharmacopeia", "JPC", "USP", "NF" and "EP", including antipyretic analgesics, drugs for the nervous system, hypnotics and sedatives, muscle relaxants, blood pressure hardeners, antihistamines and the like, such as acetaminophen, ibuprofen, benzoic acid, ethenzamide, caffeine, camphor, quinine, calcium gluconate, dimercaprol, sulfamine, theophylline, theobromine, riboflavin, mephenesin, phenobarbital, aminophyllin, thioacetazone, quercetin, rutin, salicylic acid, theophylline sodium salt, pyrapital, quinine hydrochloride, irgapyrin, digitoxin, griseofulvin, phenacetin or the like; antibiotics such as acetylspiramycin, ampicillin, erythromycin, kisatamycin, chloramphenicol, triacetyloleandomycin, nystatin, colistin sulfate or the like; steroid hormones such as methyltestosterone, methylandrostetronediol, progesterone, estradiol benzoate, ethynyl estradiol, deoxycorticosterone acetate, cortisone acetate, hydrocortisone, hydrocortisone acetate, prednisolone or the like; non-steroidal yolk hormone drugs such as dienestrol, hexastrol, diethylstilbestrol, diethylstilbesterol dibrohionate, chlorotrianisene or the like. These medicinal ingredients may be used alone, or in combination of two or more. When the medicinal ingredient is poorly soluble in water, it can exhibit an effect irrespective of the degree of sublimation and surface polarity by being blended in the tablet of the present invention.

The active ingredient may be a poorly water-soluble oily or liquid form. Examples of the poorly water-soluble oily or liquid active ingredient include pharmaceutical medicinal ingredients described in "Japanese Pharmacopeia", "JPC", "USP", "NF", or "EP", including vitamins such as teprenone, indomethacin farnesyl, menatetrenone, phytonadione, vitamin A oil, fenipentol, vitamin D, vitamin E or the like; higher unsaturated fatty acids such as DHA (docosahexaenoic acid), EPA (eicosapentaenoic acid), liver oil or the like; coenzyme Qs; oil-soluble flavorings such as orange, lemon, peppermint oils or the like; and the like. For vitamin E, there are various homologues and derivatives thereof, which are used in the present invention without particular restriction if they are in liquid form at ordinary temperature. Examples thereof include dl-α-tocopherol, dl-α-tocopherol acetate, d-α-tocopherol, d-α-tocopherol acetate and the like. These active ingredients may be used alone, or in combination of two or more.

The active ingredient may be a poorly water-soluble semi-solid active ingredient. Examples of the poorly water-soluble semi-solid active ingredient include Chinese herbal medicines or crude drug extracts such as earthworm, licorice, cassia bark, peony root, moutan bark, Japanese valerian, zanthoxylum fruit, ginger, citrus unshiu peel, ephedra herb, nandina fruit, yellow bark, polygala root, platycodon root, plantago seed, plantago herb, shorttube lycoris, senega root, fritillaria bulb, fennel, phellodendron bark, coptis rhizome, zedoary, matricaria, gentian, oriental bezoar, beast gall, adenophorae radix, ginger, *Atractylodes lancea* rhizome, clove, citrus unshiu peel, atractylodes rhizome, panax rhizome, ginseng, kakkonto, keihito, kousosan, saikokeishito, shosaikoto, shoseiryuto, bakumondoto, hangekobokuto, maoto or the like; an oyster meat extract, propolis or extract thereof, coenzyme Qs and the like. These active ingredients may be used alone, or in combination of two or more.

The active ingredient may be a sublimation one. Examples of the sublimation active ingredient include sublimation medicinal ingredients of pharmaceutical product described in "Japanese Pharmacopeia", "JPC", "USP", "NF", or "EP", including benzoic acid, ethenzamide, caffeine, camphor, salicylic acid, phenacetin, ibuprofen and the like. These active ingredients may be used alone, or in combination of two or more. As used herein, the sublimation ingredient described in this specification is not particularly limited provided that it has sublimation, and it may be any state of solid, liquid or semi-solid at ordinary temperature.

These active ingredients may be blended in the tablet of the present embodiment together with the cellulose powder of the present embodiment in a finely pulverized state. For example, the active ingredient used in the present specification may be finely pulverized to particles having an average particle size of 1 µm or more and 40 µm or less for the purpose of improving the dispersibility of active ingredient or improving the mixing uniformity of active ingredient having medicinal effects and contained in a small amount. The average particle size of the active ingredient is more preferably 1 µm or more and 20 µm or less, and even more preferably 1 µm or more and 10 µm or less.

[Other Additives]

The tablet of the present embodiment may contain other additives in addition to the above-mentioned cellulose powder and poorly water-soluble medicinal ingredient. Examples of said other additives include excipients, disintegrants, binders, fluidizing agents, lubricants, flavoring agents and the like.

Examples of the excipient include those classified as an excipient in "Japanese Pharmaceutical Excipients Directory" (published by Yakuji Nippo, LTD.), such as acrylated starch, L-asparagic acid, aminoethyl sulfonic acid, aminoacetate, wheat gluten (powder), gum arabic, powdered acacia, alginic acid, sodium alginate, pregelatinized starch, light gravel granule, inositol, ethyl cellulose, ethylene-vinyl acetate copolymer, sodium chloride, olive oil, kaolin, cacao butter, casein, fructose, light gravel granule, carmellose, carmellose sodium, silicon dioxide hydrate, dry yeast, dried aluminum hydroxide gel, dried sodium sulfate, dried magnesium sulfate, agar, agar powder, xylitol, citric acid, sodium citrate, disodium citrate, glycerin, calcium glycerophosphate, sodium gluconate, L-glutamine, clay, clay 3, clay grain, croscarmellose sodium, crospovidone, magnesium aluminosilicate, calcium silicate, magnesium silicate, light silicic anhydride, light liquid paraffin, cinnamon powder, crystalline cellulose, crystalline cellulose-carmellose sodium, crystalline cellulose (grain), brown rice malt, synthetic aluminum silicate, synthetic hydrotalcite, sesame oil, wheat flour, wheat starch, wheat germ powder, rice powder, rice starch, potassium acetate, calcium acetate, cellulose acetate phthalate, safflower oil, white beeswax, zinc oxide, titanium oxide, magnesium oxide, β-cyclodextrin, dihydroxyaluminum aminoacetate, 2,6-dibutyl-4-methylphenol, dimethylpolysiloxane, tartaric acid, potassium hydrogen tartrate, plaster, sucrose fatty acid ester, alumina magnesium hydroxide, aluminum hydroxide gel, aluminum hydroxide/sodium hydrogen carbonate coprecipitate, magnesium hydroxide, squalane, stearyl alcohol, stearic acid, calcium stearate, polyoxyl stearate, magnesium stearate, soybean hardened oil, purified gelatine, purified shellac, purified sucrose, purified sucrose spherical granulated powder, cetostearyl alcohol, polyethylene glycol 1000 monocetyl ether, gelatine, sorbitan fatty acid ester, D-sorbitol, tricalcium phosphate, soybean oil, unsaponified soy bean, soy bean lecithin, powdered skim milk, talc, ammonium carbonate, calcium carbonate, magnesium carbonate, neutral anhydrous sodium sulfate, low substitution degree hydroxypropylcellulose, dextran, dextrin, natural aluminum silicate, corn starch, powdered tragacanth, silicon dioxide, calcium lactate, lactose, lactose granulated substance, par filler 101, white shellac, white vaseline, white clay, sucrose, sucrose/starch spherical granulated powder, naked barley green leaf extract, dried powder of bud and leaf juice of naked barley, honey, paraffin, potato starch, semi-digested starch, human serum albumin, hydroxypropyl starch, hydroxypropylcellulose, hydroxypropylcellulose, hydroxypropyl methylcellulose phthalate, hydroxypropyl methylcellulose phthalate, phytic acid, glucose, glucose hydrate, partially pregelatinized starch, pullulan, propylene glycol, starch syrup of reduced malt sugar powder, powdered cellulose, pectin, bentonite, sodium polyacrylate, polyoxyethylene alkyl ethers, polyoxyethylene hydrogenated castor oil, polyoxyethylene (105) polyoxypropylene (5) glycol, polyoxyethylene (160) polyoxypropylene (30) glycol, sodium polystyrene sulfonate, polysorbate 80, polyvinylacetal diethylamino acetate, polyvinylpyrrolidone, polyethylene glycol, maltitol, maltose, D-mannitol, water candy, isopropyl myristate, anhydrous lactose, anhydrous calcium hydrogenphosphate, anhydrous calcium phosphate granulated substance, magnesium aluminometasilicate, methyl cellulose, cottonseed powder, cotton oil, haze wax, aluminum monostearate, glyceryl monostearate, sorbitan monostearate, pharmaceutical carbon, peanut oil, aluminum sulfate, calcium sulfate, granular corn starch, liquid paraffin, dl-malic acid, calcium monohydrogen phosphate, calcium hydrogenphosphate, calcium hydrogenphosphate granulated substance, sodium hydrogenphosphate, potassium dihydrogen phosphate, calcium dihydrogen phosphate, sodium dihydrogenphosphate or the like; and the like. These excipients may be used alone, or in combination of two or more.

Examples of the disintegrant include those classified as disintegrants in "Japanese Pharmaceutical Excipients Directory" (published by Yakuji Nippo, LTD.), such as celluloses such as croscarmellose sodium, carmellose, carmellose calcium, carmellose sodium, low substitution degree hydroxypropylcellulose or the like; starches such as sodium carboxymethyl starch, hydroxypropyl starch, rice starch, wheat starch, corn starch, potato starch, partially pregelatinized starch or the like; synthetic polymers such as crospovidone, crospovidone copolymer or the like; and the like. These disintegrants may be used alone, or in combination of two or more. Examples of the binder include those classified as binders in "Japanese Pharmaceutical Excipients Directory" (published by Yakuji Nippo, LTD.), such as saccharides such as sucrose, glucose, lactose and fructose, sugar alcohols such as mannitol, xylitol, maltitol, erythritol, sorbitol or the like; water-soluble polysaccharides such as gelatine, pullulan, carrageenan, locust bean gum, agar, glucomannan, xanthan gum, tamarind gum, pectin, sodium alginate, Arabia gum or the like; celluloses such as crystalline cellulose, powdered cellulose, hydroxypropylcellulose, methyl cellulose or the like, starches such as pregelatinized starch, starch paste or the like; synthetic polymers such as polyvinylpyrrolidone, carboxyvinyl polymer, polyvinyl alcohol or the like, inorganic compounds such as calcium hydrogenphosphate, calcium carbonate, synthetic hydrotalcite, magnesium aluminosilicate or the like, and the like. These binders may be used alone, or in combination of two or more.

Examples of the fluidizing agent include those classified as fluidizing agents in "Japanese Pharmaceutical Excipients Directory" (published by Yakuji Nippo, LTD.), such as silicon compounds such as silicon dioxide hydrate, light silicic anhydride or the like; and the like. These fluidizing agents may be used alone, or in combination of two or more.

Examples of the lubricant include those classified as lubricants in "Japanese Pharmaceutical Excipients Directory" (published by Yakuji Nippo, LTD.), such as magnesium stearate, calcium stearate, stearic acid, sucrose fatty acid ester, talc or the like; and the like. These lubricants may be used alone, or in combination of two or more.

Examples of the taste-masking agent include those classified as taste-masking agents in "Japanese Pharmaceutical Excipients Directory" (published by Yakuji Nippo, LTD.), such as glutamic acid, fumaric acid, succinic acid, citric acid, sodium citrate, tartaric acid, malic acid, ascorbic acid, sodium chloride, 1-menthol or the like; and the like. These taste-masking agents may be used alone, or in combination of two or more.

Examples of the flavoring agent include those classified as flavoring agents in "Japanese Pharmaceutical Excipients Directory" (published by Yakuji Nippo, LTD.), such as orange, vanilla, strawberry, yogurt, menthol, oils such as fennel oil, cinnamon bark oil, orange peel oil, peppermint oil or the like; green tea powder, or the like; and the like. These flavoring agents may be used alone, or in combination of two or more.

Examples of the coloring agent include those classified as coloring agents in "Japanese Pharmaceutical Excipients Directory" (published by Yakuji Nippo, LTD.), such as edible dyes such as edible red 3, edible yellow 5 and edible blue 1, sodium copper chlorophyllin, titanium oxide, riboflavin or the like, and the like. These coloring agents may be used alone, or in combination of two or more.

Examples of the sweetener include those classified as sweeteners in "Japanese Pharmaceutical Excipients Directory" (published by Yakuji Nippo, LTD.), such as aspartame, saccharin, dipotassium glycyrrhizinate, stevia, maltose, maltitol, starch syrup, powdered sweet hydrangea leaf or the like; and the like. These sweeteners may be used alone, or in combination of two or more.

<Method for Producing Tablet>

The tablet of the present embodiment can be produced, for example, using the method shown below. The method for producing a tablet shown below is an example, and the effects of the present embodiment are not limited to the following method.

Examples of the method for producing a tablet include a method in which a poorly water-soluble medicinal ingredient and cellulose are mixed and then compression-molded. At this time, in addition to the poorly water-soluble medicinal ingredient, other additives may be added as needed. Said other additives may be at least one selected from, for example, the above-mentioned excipients, disintegrants, binders, fluidizers, lubricants, taste-masking agents, flavoring agents, coloring agents, sweeteners, dissolving auxiliaries and the like.

The order of addition of each ingredient is not particularly limited and may be i) a method involving collectively mixing a poorly water-soluble medicinal ingredient, a cellulose, and, if necessary, other additives and then subjecting the mixture to compression molding or ii) a method involving premixing a poorly water-soluble medicinal ingredient and at least one additive selected from a fluidizing agent and a lubricant, then mixing a cellulose, and if necessary, other additives, followed by subjecting the mixture to compression molding. From the viewpoint of simplicity of operation, method i) is preferable. The lubricant may also be added to the mixture for compression molding obtained in method i) or method ii), which is further mixed and then subjected to compression molding. The method for adding each ingredient is not particularly limited provided that it is a commonly used method, and they may be continuously added or collectively charged using a small size suction transport apparatus, an air transport apparatus, a bucket conveyor, a pneumatic transport apparatus, a vacuum conveyer, a vibration type quantitative metering feeder, a sprayer, a funnel and the like. As the spraying method, a method involving spraying a poorly water-soluble medicinal ingredient solution/dispersion using a pressure nozzle, a two-fluid nozzle, a four-fluid nozzle, a turning disc, a supersonic wave nozzle or the like, or a method involving adding dropwise a poorly water-soluble medicinal ingredient solution/dispersion from a tube-like nozzle may be used.

The mixing method is not particularly limited provided that it is a commonly performed method and may use a vessel rotation type mixer such as V-type, W-type, double cone type and container tack type mixers, a stirring type mixer such as high-speed stirring type, universal stirring type, ribbon type, pug type and Nauta-type mixers, a high-speed fluid type mixer, a drum type mixer, and a fluidized bed type mixer. In addition, a vessel shaking type mixer such as a shaker may also be used.

The compression molding method of the composition is not particularly limited provided that it is a commonly performed method and may be a method for compressing and molding to form a desired shape with a mortar and pestle or a method for compressing and molding to form in advance a sheet to be cut into a desired form. As a compression molding machine, for example, a compressor such as a hydrostatic press, a roller type press such as a briquetting roller type press or a smoothing roller type press, a single-punch tableting machine, or a rotary tableting machine may be used.

The method for dissolving or dispersing a poorly water-soluble medicinal ingredient in a medium is not particularly limited provided that it is a commonly performed dissolution or dispersion method and may be a stirring/mixing method using a stirring blade such as a one-direction rotation type, multi-axis rotation type, reciprocal inversion type, vertical movement type, rotation+vertical movement type, and piping type such as a portable mixer, a three-dimensional mixer, and a side-wall mixer; a jet type stirring/mixing method such as a line mixer; a gas-blowing stirring/mixing method; a mixing method using a high-shear homogenizer, a high-pressure homogenizer, an ultrasonic homogenizer, or the like; a vessel shaking type mixing method using a shaker.

The solvent used in the above-described production method is not particularly limited provided that it is used in pharmaceutical preparations. For example, any one of water and organic solvents may be used. Examples of the organic solvent include those classified as solvents in "Japanese Pharmaceutical Excipients Directory" (published by Yakuji Nippo, LTD.), such as alcohols such as methanol, ethanol, isopropyl alcohol, butyl alcohol, 2-methylbutyl alcohol, benzyl alcohol or the like; hydrocarbons such as pentane, hexane, heptane, cyclohexane or the like, ketones such as acetone, ethyl methyl ketone or the like; and the like. These solvents may be used alone, or in combination of two or more, or the solid content may be dispersed once in one medium, then dispersed in a different medium after removing the medium.

When dissolving a poorly water-soluble medicinal ingredient in a medium, a solubilizer may be used as a dissolving auxiliary. Examples of the solubilizer include water-soluble polymers, fats and oils, surfactants and the like. As the water-soluble polymer, oil and fat, and surfactant used as a solubilizer, those described in the "Encyclopedia of Pharmaceutical Additives" (published by Yakuji Nippo, LTD.) and the like can be appropriately used, and specifically, the same as those exemplified above as a solubilizer can be mentioned. These solubilizers may be used alone or in combination of two or more.

Examples of the method for molding into tablets include a direct compression method which involves directly compressing and molding a mixture of a poorly water-soluble medicinal ingredient with a cellulose, or a mixture of one or more poorly water-soluble medicinal ingredients with a cellulose, and if necessary, other additives. Other production methods for a multicore tablet having as an inner core a tablet which is preliminarily compressed and molded, or a multilayer tablet in which a plurality of molded products prepared by preliminary compression are laminated and again compressed can also be used. The direct compression method is preferable from the viewpoint of productivity and ease of process control.

The compression molded tablet may be further coated. Examples of the coating agent used in this case include coating agents described in the "Encyclopedia of Pharmaceutical Additives" (published by Yakuji Nippo, LTD.). These coating agents may be used alone or in combination of two or more.

The granulation method used in the production process through granulation step includes dry granulation, wet granulation, heating granulation, spray granulation, and microencapsulation. Specifically, fluidized-bed granulation, stirring granulation, extrusion granulation, crushing granulation and tumbling granulation methods are useful as the wet granulation method. The fluidized-bed granulation method involves performing granulation by spraying a binding liquid on a fluidized powder in a fluidized-bed granulator. The stirring granulation involves simultaneously performing the mixing, kneading and granulation of the powder in a tightly-sealed structure by rotating a stirring blade in a mixing vessel while adding a binding liquid. The extrusion granulation involves performing granulation by forcibly extruding a wet mass kneaded by adding a binding liquid, through a screen in a suitable size by a screw-type or a basket-type method. The crushing granulation method involves performing granulation by shearing and crushing a wet mass kneaded by adding a binding liquid, by the rotary knife of a granulator and sputtering the sheared and crushed matter from the circumferential screen by its centrifugal force. The tumbling granulation method involves performing granulation by tumbling the powder by the centrifugal force of a revolving rotor and forcing spherical granules having a uniform particle size to be grown larger and larger by a binding liquid sprayed from a spray gun at the time of tumbling.

As the method for drying the granulated product, any of a hot-air heating type method (shelf drying, vacuum drying, and fluidized bed drying), a heat type (pan type, shelf box type, and drum type) method and lyophilization can be used. The hot air heating type method involves directly contacting additives with hot air and simultaneously removing evaporated water. The heat conduction type method involves indirectly heating additives through a heat-conducting wall. The lyophilization involves freezing additives at −10 to 40° C. and then warming them under high vacuum ($1.3 \times 10^{-5}$ to $2.6 \times 10^{-4}$ MPa) to sublimate and remove water.

<Properties of Tablet>
[Abrasion Degree]

The abrasion degree of the tablet of the present embodiment is preferably 0.5% or less, more preferably 0.4% or less, even more preferably 0.3% or less, and particularly preferably 0.2% or less, most preferably 0.1% or less.

By containing the above-mentioned cellulose, the tablet of the present embodiment can be controlled to have an abrasion degree of not more than the above-mentioned upper limit.

[Hardness]

The hardness of the tablet of the present embodiment is preferably 50 N or more, more preferably 51 N or more.

By containing the above-mentioned cellulose, the tablet of the present embodiment can be controlled to have a hardness of not more than the above-mentioned upper limit. The hardness of the tablet can be measured using the method described in Examples later.

EXAMPLE

The present embodiment will be described in detail with reference to the Examples and Comparative Examples, but the present embodiment is not limited thereto. The physical properties of the Examples and Comparative Examples and their measurement methods are as follows.

<Measurement Method of Physical Properties>
[Physical Property 1] Content of Alkali-Soluble Substance 1 g of each cellulose powder was weighed in a 50-mL plastic centrifuge tube (Nalgene™ High-Speed Round-Bottom PPCO Centrifuge Tubes, product number: 3110-0500) (here, the weight of the actually weighed cellulose powder was defined as M1 [g]). 25 mL of a 17.5 mass % sodium hydroxide aqueous solution was added at room temperature (20° C.), the aqueous solution was stirred with a spatula, and the entire cellulose powder was immersed in the sodium hydroxide aqueous solution and allowed to stand. After 30 minutes had passed from the addition of the sodium hydroxide aqueous solution, 10 mL of distilled water was added, stirred with a spatula, and allowed to stand for 5 minutes. Next, the aqueous solution was centrifuged (centrifugal force: 15000 G, time: 20 minutes, temperature: 20° C., accel: rapid, decel: rapid) to precipitate the solid content, and 20 mL of the supernatant was sucked up with a dropper and discarded. 25 mL of distilled water was added to the remaining precipitate and solution and stirred with a spatula. Then, the aqueous solution was centrifuged (15000 G×20 minutes) to precipitate the solid content, and 25 mL of the supernatant was discarded. After performing the above washing operation twice more, 25 mL of a 10 mass % acetic acid aqueous solution was added and stirred with a spatula to adjust the liquid property to acidic. Next, the prepared solution was suction-filtered with a 1G3 glass filter whose mass (T1 [g]) at the time of drying had been measured in advance. The solid matter remaining on the glass filter was washed with 40 mL of a 10 mass % acetic acid aqueous solution, and then washed with 500 mL of boiling water (98° C.). The washed powder (solid matter) was placed in an oven at 105° C. together with the glass filter and dried for 6 hours or more. The powder and the glass filter were taken out from the oven, placed in a desiccator containing silica gel as a desiccant, cooled to room temperature, and the mass (W1 [g]) was measured.

Further, in the above test, a blank test was performed using distilled water instead of the 17.5 mass % sodium hydroxide aqueous solution. In the blank test, the weight of the cellulose actually weighed was defined as MB [g], the mass of the glass filter was defined as TB [g], and the mass of the powder was defined as WB [g]. Using the obtained M1, T1, W1, MB, TB and WB, the content (%) of the alkali-soluble substance was calculated by the formula shown below. For each cellulose powder, the alkali-soluble substance was measured twice or more, and the average value was used.

Alkali-soluble substance content (%)={(W1−T1) [g]/ M1 [g]−(WB−TB) [g]/MB [g]}×100

[Physical Property 2] Average Particle Size of Cellulose Powder

The average particle size of the cellulose powder was measured using a laser diffraction type particle size distribution meter (trade name: LA-950 V2, manufactured by HORIBA, Ltd.) in a dry measurement mode with a compressed air pressure of 0.10 MPa, a feeder speed of 160, a feeder initial velocity coefficient of 1.2 and a refractive index of 1.51. The particle size at a cumulative volume of 50% obtained by the measurement was taken as the average particle size (μm) of the cellulose powder.

[Physical Property 3] Aerated Bulk Density of Cellulose Powder

For the measurement, a cellulose powder having a water content adjusted to 3.5% by mass or more and 4.5% by mass or less was used. When the water content range of the cellulose powder was out of the lower range, the water content was adjusted by allowing the cellulose powder to absorb water in a constant temperature/humidity chamber or the like. When the water content range of the cellulose powder was out of the upper range, hot air at 60° C. was evenly applied to the cellulose powder using a hot air oven to adjust the water content within the range.

A Scott volume meter (model: ASTM B-329-85, manufactured by Tsutsui Rikagaku Kikai) was used to measure the aerated bulk density of the cellulose powder, and the cellulose powder was filled in a 25 cc-cylindrical metal container through a sieve (opening: 1 mm). The cellulose powder contained in the 25 cc-cylindrical metal container was scraped off, and the mass (g) of the cellulose powder contained in the container was divided by 25 cc to determine the aerated bulk density. The measurement was carried out 5 times and the average value was calculated.

[Physical Property 4] Packed Bulk Density of Cellulose Powder

For the measurement, a cellulose powder having a water content adjusted to 3.5% by mass or more and 4.5% by mass or less was used. The water content of the cellulose powder was adjusted so as to fall within the range by using the method described in "Physical property 3". The packed bulk density (hard apparent specific gravity) (g/cc) was calculated with a powder physical property measuring machine (PT-R, manufactured by Hosokawa Micron). The sieve used had a mesh opening of 710 μm, and the funnel was made of metal (coated with antistatic spray) and had an inner diameter of 0.8 cm. VIBRATION was carried out at 2.0 (power supply: AC100V, 60 Hz).

[Physical Property 5] Compression Ratio of Cellulose Powder

The compression ratio of each cellulose powder was calculated by the formula shown below.

Compression degree (%)=([Packed bulk density]− [Aerated bulk density])/[Packed bulk density]× 100

[Physical Property 6] Whiteness of Cellulose Powder

A spectroscopic colorimeter (SE-2000, manufactured by Nippon Denshoku Kogyo) was used to obtain the values of brightness (L), saturation (green to red) (a) and saturation (blue to yellow) (b), and calculate the whiteness by the formula shown below.

Whiteness=100−[(100−L)$^2$+(a$^2$+b$^2$)]$^{0.5}$

[Physical Property 7] Water Absorption Amount of Cellulose Powder 2 g of the cellulose powder was weighted in a 50-mL plastic centrifuge tube (Nalgene™ High-Speed Round-Bottom PPCO Centrifuge Tubes, product number: 3110-0500) (the mass actually weighed was defined as "Wi" [g]), 30 mL of pure water was added, and the resulting mixture was dispersed while stirring with a spatula, so as to entirely immerse the cellulose powder in the pure water. After standing the resulting mixture for 30 minutes, the solid content was precipitated by centrifugation ((inverter/compact high-speed cooling centrifuge, manufactured by Kubota Seisakusho, model: 6930, angle rotor RA-400, centrifugal force: 7500 G, time: 10 minutes, temperature: 20° C., accel: rapid, decel: rapid). The opening of the centrifuge tube was tilted downward so as not to break the precipitated cellulose layer, thereby removing the supernatant, and the opening of the centrifuge tube was tilted downward by 30° from the horizontal and allowed to stand for 5 minutes on a table laid with a paper towel to drain the excess water. Next, the mass (Wf [g]) of the water-absorbed cellulose powder was measured.

Using the obtained Wi and Wf, the water absorption amount (%) can be calculated by the formula shown below. The water absorption amount of each cellulose powder was measured twice or more, and the average value was used.

Water absorption amount (%)=(Wf−Wi)/Wi×100

[Physical Property 8] Particle Size of Primary Particles of Cellulose Powder 0.5 g of cellulose powder was placed in 10 mL of pure water, and ultrasonic irradiation (600 W, 40 kHz) was performed for 10 minutes. Then, a laser diffraction type particle size distribution meter (trade name: LA-950 V2, manufactured by Horiba Seisakusho) was used to measure the particle size in the wet measurement mode with a refractive index of 1.20 (cellulose refractive index: 1.59, water refractive index: 1.33), pretreatment conditions (ultrasonic irradiation 1 minute, ultrasonic intensity 1), a circulation speed of 7, and a stirring speed of 5. The particle size at 50% of cumulative volume particles obtained by the measurement was defined as the average particle size (μm) of primary particles of the cellulose.

[Physical Property 9] Ratio of Major Axis to Minor Axis of Cellulose Particles (L/D)

Cellulose powder was dispersed on a glass plate and photographed with a microscope (VHX-1000, manufactured by KEYENCE) at a magnification of 500 times. The captured image was analyzed by the following procedure using an image processing analysis system software (Image HyperII, manufactured by DigiMo), and the aspect ratio of the particles (ratio of major axis to minor axis: L/D) was measured. The measurements were carried out on at least 50 particles and the average value was calculated.

(1) Step 1: Binarization Process

The image taken with the microscope was captured in monochrome analysis software, and the scale of the image was set by the two-point distance method. Next, the "Otsu method" was selected in the binarization process, and the threshold value was set. Since the optimum threshold value differs for each image, the threshold value was selected so as to match the shape of the original particle as much as possible while comparing with the original image.

(2) Step 2: Binarization Manual Correction

While comparing with the original image taken, particles that did not give appropriate measurement results, such as particles that overlapped each other, particles that protruded from the screen, particles that were unclear and had blurred outlines, and the like, were deleted and excluded from the measurement target.

(3) Step 3: Hole Filling

In "hole filling" mode, "8" was selected for "neighborhood" and "hole filling" was executed. Next, the image was compared with the original image again in "binary image manual correction", and it was confirmed whether the correction was performed normally. If the correction was not performed normally, the manual correction was performed again.

(4) Step 4: Image Measurement

After setting the number of deleted pixels to "100" and selecting "8" for "neighborhood", "image measurement" was executed. The measurement results of "major diameter" and "minor diameter" for each particle to be measured were displayed on a personal computer. The value obtained by dividing "major axis" by "minor axis" was used as the aspect ratio.

[Physical Property 10] Repose Angle of Cellulose Powder

For the measurement, a cellulose powder having a water content adjusted to 3.5% by mass or more and 4.5% by mass or less was used. The water content of the cellulose powder was adjusted so as to fall within the range by using the method described in "Physical Properties 3".

For the measurement of repose angle of the cellulose powder, a Sugihara-type repose angle measuring device (slit size: depth 10×width 50×height 140 mm, a protractor installed at a position of width 50 mm) was used. The cellulose powder was dropped into the slit at a rate of 50 cc/min with a quantitative feeder to deposit the cellulose powder on the bottom of the apparatus. The deposited cellulose powder gradually formed a slope, and the addition of the cellulose powder was continued until the slope formed a stable angle. When the charged cellulose powder formed a stable slope, the angle between this slope and the bottom of the device was read. This angle is the repose angle of the cellulose powder. The measurement was carried out 5 times and the average value was calculated.

<Evaluation Method>

Tablets obtained by compression molding only cellulose powder with a compressor (hereinafter, sometimes abbreviated as "MCC simple tablets") and orally disintegrating tablets (hereinafter, sometimes abbreviated as "OD tablets") were prepared. Various evaluations were performed.

[Preparation of MCC Simple Tablets]

For tableting, a cellulose powder having a water content adjusted to about 4% by mass was used. The water content of the cellulose powder was adjusted so as to fall within the range by using the method described in "Physical properties 3". A tableting machine (1325VCW, manufactured by Aiko Engineering) equipped with a flat punch having a diameter of 1.13 cm (bottom area: 1 cm$^2$) (manufactured by Kikusui Seisakusho, using materials SUK2, 3) and a mortar (manufactured by Kikusui Seisakusho, using materials SUK2, 3) was used to carry out the tableting operation. Specifically, 500 mg of the powder was placed in the mortar, compressed with the tableting machine at 1 kN and 3 kN, and held at that stress for 10 seconds to prepare the tablets. The prepared tablets were placed in a plastic bag with a zipper, sealed and stored at room temperature so as not to absorb moisture until the hardness was measured.

[Preparation of OD Tablets]

The formulation powder shown below was placed in a plastic bag, shaken for 1 minute to mix, and sieved through a 710 μm sieve. Further, a lubricant (stearyl fumarate) was added to the formulation powder so as to be 1% by mass with respect to the total mass of the tablets, followed by mixing for 30 seconds. Next, the mixed powder was tableted with a rotary tableting machine (manufactured by Kikusui Seisakusho, Clean Press Collect 12HUK, 12 punches, turntable: 54 rpm) to obtain 200 mg of a Φ8 mm-12R tablets. The tableting pressure was appropriately set so that the tablet hardness was 60 N or more and 70 N or less.

(Formulation)

Mannitol for direct compression (Mannitol EZ, manufactured by Asahi Kasei): 70% by mass Partially pregelatinized starch (PCS, PC-10, manufactured by Asahi Kasei): 10% by mass Croscarmellose sodium (Kiccolate ND-200, manufactured by Asahi Kasei): 5% by mass Cellulose powder: 15% by mass The above content is an amount with respect to the total mass of the tablet.

[Evaluation 1] Hardness

The hardness of each tablet was measured with a hardness tester (DR. SCHLEUNIGER Tablet Tester 8M) after 20 hours or more and 48 hours or less had elapsed immediately after tableting. The average value of five tablets at each tableting pressure was taken as the hardness of tablets.

[Evaluation 2] Disintegration Property

The disintegration property of each tablet was examined according to "disintegration testing method" (the general test method) (test solution: water, with disc) described in the 17th revised Japanese Pharmacopoeia. An integration test container (trade name: NT-40HS type, manufactured by Toyama Sangyo) was used to determine the integration time in pure water at 37° C. The average value of 6 tablets was taken as the tablet disintegration time.

[Evaluation 3] Texture

With three healthy adult males as panelists, the tablet-taking feeling in the oral cavity was sensually evaluated on each OD tablet. The case where a powdery texture was felt was determined as "with dry feeling", the case where a powdery texture was not felt was determined as "no dry feeling", the case where the core remained in the oral cavity when the tablet was disintegrated was determined as "with core-remaining", and the case where the core did not remain in the oral cavity when the tablet was disintegrated was determined as "without core-remaining". The measurement was performed twice for each person, for example, in a case where a panelist did not feel anything the first time, and felt a dry feeling the second time, the evaluation of that panelist was determined as "with dry feeling", and in a case where "core-remaining" was felt even once, it was determined as "with core-remaining".

[Evaluation 4] Mount-Generation Property

Tablets having the following formulations were prepared and the mount-generation property was evaluated by an elution test.

Formulation: Mannitol EZ for direct compression/Cellulose powder=85% by mass/15% by mass Tableting: Tableting machine (1325VCW, manufactured by Aiko Engineering), Φ8 mm-12R, 200 mg tablet The tableting pressure was adjusted so that the tablet hardness was 45 N or more and 55 N or less.

The elution testing method was based on the "Japanese Pharmacopoeia elution testing method", and one tablet was added under the conditions of 900 ml of water, 37° C., and a paddle rotation speed of 50 rpm. Twenty minutes after the tablet was added, the inside of the elution test vessel was observed, and the formation of mount on the bottom of the vessel was evaluated according to the evaluation criteria shown below.

(Evaluation Criteria)

⊚: Mount with a diameter of less than 3 mm were generated, or no mount was generated o: Mount with a diameter of 3 mm or more and less than 7 mm was generated x: Mount with a diameter of 7 mm or more was generated

[Evaluation 4] Elution Rate (1) Elution Test of Itraconazole Tablets

The elution test of an itraconazole tablet was performed according to the Japanese Pharmacopoeia elution testing method The elution rate under the following conditions was measured. Paddle rotation speed: 50 rpm; Test solution: elution test solution 1 (pH 1.2) of the Japanese Pharmacopoeia; Elution time: 60 minutes (required level: 50% or more of elution rate), 120 minutes (required level: 75% or more of elution rate). The elution rate of the drug was measured by HPLC under the following measurement conditions.

(Measurement Condition)

Detector: Ultraviolet absorptiometer (measurement wavelength: 225 nm)

Column: Octadecylsilylated silica gel column for liquid chromatography with an inner diameter of 4.6 mm and a length of 10 cm Column temperature: 30° C.

Mobile phase A: Tetrabutylammonium hydrogensulfate solution (concentration: 0.08 mol %, 17 g of tetrabutylammonium hydrogensulfate was dissolved in water to prepare 625 g of aqueous solution)

Mobile phase B: acetonitrile

Liquid transfer of mobile phase: The concentration gradient was controlled by changing the mixing ratio of the mobile phase A and the mobile phase B as follows. 0-20 minutes immediately after injection (A/B: 80/20→50/50), 20-25 minutes (A/B: 50/50), flow rate: 1.5 mL per minute (2) Elution Test of Acetazolamide Tablets The elution test of acetazolamide tablets was performed according to the Japanese Pharmacopoeia elution testing method Paddle method.

The elution rate under the following conditions was measured. Paddle rotation speed: 50 rpm; Test solution: elution test solution 1 (pH 1.2) of the Japanese Pharmacopoeia; Elution time: 90 minutes (required level: 75% or more of elution rate). The elution rate of the drug was measured by measuring the absorbance of the test solution (265 nm, Japanese Pharmacopoeia elution test 1 solution).

<Preparation of Cellulose Powder>

[Example 1-1] Preparation of Cellulose Powder A (1) Preparation of Wet Flock X 2 kg of shredded commercially available SP pulp and 30 L of hydrochloric acid aqueous solution were placed in a low-speed stirrer (trade name: 30 LGL reactor, manufactured by Ikebukuro Ryo Kogyo Co., Ltd.). The resulting mixture was hydrolyzed while stirring (reaction conditions: hydrochloric acid concentration: 0.05%, reaction temperature: 80° C., reaction time: 6 hours, stirring speed: 5 rpm) to obtain an acid-insoluble residue. The obtained acid-insoluble residue was thoroughly washed with pure water until the electrical conductivity of the filtrate became less than 100 µS/cm, and then filtered to obtain wet flock X.

(2) Preparation of Wet Flock Y

Separately, 2 kg of shredded commercially available SP pulp and 30 L of hydrochloric acid aqueous solution were placed in a low-speed stirrer (trade name: 30 LGL reactor, manufactured by Ikebukuro Ryo Kogyo Co., Ltd.). The resulting mixture was hydrolyzed while stirring (reaction conditions: hydrochloric acid concentration: 1.0%, reaction temperature: 130° C., reaction time: 2 hours, stirring speed: 220 rpm) to obtain an acid-insoluble residue. The obtained acid-insoluble residue was thoroughly washed with pure water until the electrical conductivity of the filtrate became less than 100 µS/cm, and then filtered to obtain wet flock Y.

(3) Preparation of Cellulose Powder A

Wet flock X and wet flock Y were mixed at 60:40 (solid content mass ratio) and introduced into a 90-L poly bucket. Pure water was then added so that the total solid content concentration was 25% by mass. The resulting mixture was then neutralized with aqueous ammonia while stirring with a three-one motor (pH was 7.5 or more and 8.0 or less after neutralization), followed by spray drying the resulting mixture (conditions: supply rate of dispersion liquid: 6 kg/hour, inlet temperature: 180° C. or higher 220° C. or lower, outlet temperature: 50° C. or higher and 70° C. or lower) to obtain cellulose powder A.

[Example 1-2] Preparation of Cellulose Powder B

Cellulose powder A obtained in Example 1-1 was pulverized with a jet mill (pulverizing pressure: 0.4 MPa) to obtain cellulose powder B.

[Example 1-3] Preparation of Cellulose Powder C

Cellulose powder C was obtained by the same method as in Example 1-1 except wet flock X and wet flock Y were mixed at a ratio of 50:50 (solid content mass ratio).

[Examples 1 to 4] Preparation of Cellulose Powder D

Cellulose powder C obtained in Examples 1 to 3 was pulverized with a jet mill (pulverizing pressure: 0.4 MPa) to obtain cellulose powder D.

[Example 1-5] Preparation of Cellulose Powder E

Cellulose powder E was obtained by the same method as in Example 1-1 except that wet flock X and wet flock Y were mixed at a ratio of 40:60 (solid content mass ratio).

[Example 1-6] Preparation of Cellulose Powder F

Cellulose powder E obtained in Examples 1-5 was pulverized with a jet mill (pulverizing pressure 0.4 MPa) to obtain cellulose powder F.

[Example 1-7] Preparation of Cellulose Powder G 2 kg of shredded commercially available SP pulp and 30 L of hydrochloric acid aqueous solution were placed in a low-speed stirrer (trade name: 30 LGL reactor, manufactured by Ikebukuro Ryo Kogyo Co., Ltd.). The resulting mixture was hydrolyzed while stirring (reaction conditions: hydrochloric acid concentration: 0.5%, reaction temperature: 130° C., reaction time: 2 hours, stirring speed: 350 rpm) to obtain an acid-insoluble residue. The obtained acid-insoluble residue was thoroughly washed with pure water until the electrical conductivity of the filtrate became less than 100 uS/cm, and then filtered to obtain a wet flock. The obtained wet flock was introduced into a 90-L poly bucket. Pure water was then added so that the total solid content concentration was 25% by mass. The resulting mixture was then neutralized with aqueous ammonia while stirring with a three-one motor (pH was 7.5 or more and 8.0 or less after neutralization), followed by spray drying the resulting mixture (conditions: supply rate of dispersion liquid: 6 kg/hour, inlet temperature: 180° C. or higher 220° C. or lower, outlet temperature: 50° C. or higher and 70° C. or lower) to obtain cellulose powder G.

[Comparative Example 1-1] Preparation of Cellulose Powder H

Cellulose powder H was obtained by the same method as in Example 1-1 except that wet flock X and wet flock Y were mixed at 100:0 (solid content mass ratio).

[Comparative Example 1-2] Preparation of Cellulose Powder I

Cellulose powder I was obtained in the same manner as in Example 1-1 except that wet flock X and wet flock Y were mixed at a ratio of 0:100 (solid content mass ratio).

[Comparative Example 1-3] Preparation of Cellulose Powder J 2 kg of shredded commercially available SP pulp and 30 L of hydrochloric acid aqueous solution were placed in a low-speed stirrer (trade name: 30 LGL reactor, manufactured by Ikebukuro Ryo Kogyo Co., Ltd.). The resulting mixture was hydrolyzed while stirring (reaction conditions: hydrochloric acid concentration: 0.2%, reaction temperature: 110° C., reaction time: 2 hours, stirring speed: 80 rpm) to obtain an acid-insoluble residue. The obtained acid-insoluble residue was thoroughly washed with pure water until the electrical conductivity of the filtrate became less than 100 uS/cm, and then filtered to obtain a wet flock. The obtained wet flock was introduced into a 90-L poly bucket. Pure water was then added so that the total solid content concentration was 25% by mass. The resulting mixture was then neutralized with aqueous ammonia while stirring with a three-one motor (pH was 7.5 or more and 8.0 or less after neutralization), followed by spray drying the resulting mixture (conditions: supply rate of dispersion liquid: 6 kg/hour, inlet temperature: 180° C. or higher 220° C. or lower, outlet temperature: 50° C. or higher and 70° C. or lower) to obtain cellulose powder J.

The preparation conditions of cellulose powders A to J are shown in Table 1 below. Moreover, the physical properties of the obtained cellulose powders A to J were evaluated by the method described above. The results are shown in Tables 2 and 3.

TABLE 1

|  | Cellulose powder | Reaction temperature [° C.] | Reaction time [h] | Stirring speed [rpm] | Wet flock X | Wet flock Y | Cellulose dispersion concentration before spray drying | Jet mill pulverization |
|---|---|---|---|---|---|---|---|---|
| Ex. 1-1 | A |  |  |  | 60 | 40 | 6% |  |
| Ex. 1-2 | B |  |  |  | 60 | 40 | 6% | ○ |
| Ex. 1-3 | C |  |  |  | 50 | 50 | 15% |  |
| Ex. 1-4 | D |  |  |  | 50 | 50 | 15% | ○ |
| Ex. 1-5 | E |  |  |  | 40 | 60 | 8% |  |
| Ex. 1-6 | F |  |  |  | 30 | 70 | 20% | ○ |
| Ex. 1-7 | G | 130 | 2 | 350 | — | — | 15% |  |
| Ex. 1-1 | H |  |  |  | 100 | 0 | 5% |  |
| Com. Ex. 1-2 | I |  |  |  | 0 | 100 | 20% |  |
| Com. Ex. 1-3 | J | 110 | 2 | 80 | — | — | 6% |  |

TABLE 2

| | Cellulose powder | alkali-soluble substance | Average particle size [μm] | Aerated bulk density [g/cc] | Packed bulk density [g/cc] | Compression ratio [—] | Whiteness [—] | Water Absorption amount [%] | Average particle size of primary particles [μm] | L/D [—] | Repose angle [°] |
|---|---|---|---|---|---|---|---|---|---|---|---|
| Ex. 1-1 | D | 32% | 51 | 0.12 | 0.28 | 57% | 97 | 350 | 27 | 3.5 | 58 |
| Ex. 1-2 | B | 33% | 18 | 0.13 | 0.38 | 66% | 97 | 330 | 17 | 3.3 | >60 |
| Ex. 1-3 | C | 35% | 57 | 0.24 | 0.38 | 37% | 96 | 260 | 25 | 2.8 | 44 |
| Ex. 1-4 | D | 36% | 16 | 0.21 | 0.41 | 49% | 96 | 240 | 16 | 2.7 | >60 |
| Ex. 1-5 | E | 41% | 64 | 0.21 | 0.31 | 32% | 96 | 230 | 25 | 2.0 | 41 |
| Ex. 1-6 | F | 44% | 17 | 0.29 | 0.57 | 49% | 95 | 160 | 17 | 1.9 | >60 |
| Ex. 1-7 | G | 37% | 118 | 0.27 | 0.38 | 29% | 96 | 240 | 29 | 1.8 | 38 |
| Com. Ex. 1-1 | H | 10% | 43 | 0.09 | 0.24 | 63% | 98 | 390 | 30 | 3.8 | >60 |
| Com. Ex. 1-2 | I | 60% | 65 | 0.35 | 0.44 | 20% | 94 | 150 | 17 | 1.8 | 35 |
| Com. Ex. 1-3 | J | 25% | 48 | 0.08 | 0.20 | 60% | 97 | 370 | 29 | 3.6 | >60 |

TABLE 1-3

| | Cellulose powder | MCC simple tablet | | | | OD tablet | | | | Generation of mount Tablet containing 30 mg of MCC (50 rpm) |
|---|---|---|---|---|---|---|---|---|---|---|
| | | Hardness [N] | | Disintegration [S] | | | | Texture | | |
| | | 1 kN of tableting Pressure | 3 kN of tableting pressure | 1 kN of tableting pressure | 3 kN of tableting pressure | Tableting [KN] | Disintegration [S] | With or without dry feeling | With or without Core-remaining | |
| Ex. 1-1 | A | 121 | 301 | 150 | 320 | 6.0 | 20 | without | without | ○ (small mount) |
| Ex. 1-2 | B | 127 | 311 | 148 | 308 | 5.5 | 18 | without | without | ◉ (not generated) |
| Ex. 1-3 | C | 72 | 203 | 79 | 256 | 7.0 | 18 | without | without | ◉ (not generated) |
| Ex. 1-4 | D | 68 | 240 | 74 | 243 | 6.5 | 15 | without | without | ◉ (not generated) |
| Ex. 1-5 | E | 64 | 202 | 44 | 178 | 7.0 | 16 | without | without | ◉ (not generated) |
| Ex. 1-6 | F | 55 | 189 | 25 | 68 | 6.5 | 18 | without | without | ○ (small mount) |
| Ex. 1-7 | G | 48 | 164 | 43 | 122 | 7.0 | 18 | without | without | ○ (small mount) |
| Com. Ex. 1-1 | H | 186 | 452 | >1800 | >1800 | 4.0 | 41 | with | with | X (generated) |
| Com. Ex. 1-2 | I | 33 | 98 | 20 | 154 | 9.0 | 42 | without | with | X (generated) |
| Com. Ex. 1-3 | J | 182 | 479 | >1800 | >1800 | 4.0 | 37 | with | without | X (generated) |

As shown in Table 1-3, the generation of mount was suppressed in the tablets using cellulose powders A to G having an alkali-soluble substance in an amount of 32% by mass or more and 44% by mass or less. Further, in the tablets using cellulose powders B to E having the alkali-soluble substance in an amount of 33% by mass or more and 41% by mass or less, the generation of mount was particularly suppressed.

In addition, among the cellulose powders A to F, the smaller the average particle size, the shorter the disintegration time when made into tablets.

On the other hand, in the tablets using cellulose powders H to J having an alkali-soluble substance in an amount of less than 32% by mass or more than 44% by mass, mount was generated.

Example 2-1 to 2-7 and Comparative Examples 2-1 to 2-3

Using the celluloses shown in Table 2-3 below, the raw materials of the following formulations were mixed to prepare formulation powders. The formulation powders were then used to prepare tablets (9 mmφ, 250 mg/tablet) with a rotary tableting machine (tableting pressure: 5 kN). The obtained tablets were evaluated in various ways by the methods described above. The results are shown in Table 2-3.

(Formulation)

Itraconazole: 20% by mass

Cellulose: 25% by mass

Mannitol: 42% by mass

Macrogol 6000: 10% by mass

Croscarmellose sodium: 2% by mass

Magnesium stearate: 1% by mass

Examples 2-8 and Comparative Examples 2-4

Using the celluloses shown in Table 2-3 below, the raw materials of the following formulations were mixed to prepare formulation powders. The formulation powders were then used to prepare tablets (9 mmφ, 250 mg/tablet) with a rotary tableting machine. The obtained tablets were evaluated in various ways by the methods described above. The results are shown in Table 2-3.

(Formulation)

Itraconazole: 20% by mass

Cellulose: 25% by mass

Mannitol: 32% by mass

Macrogol 6000: 20% by mass
Croscarmellose sodium: 2% by mass
Magnesium stearate: 1% by mass Example 2-9 and Comparative Example 2-5

Using the celluloses shown in Table 2-3 below, the raw materials of the following formulations were mixed to prepare formulation powders. The formulation powders were then used to prepare tablets (9 mmφ, 250 mg/tablet) with a rotary tableting machine. The obtained tablets were evaluated in various ways by the methods described above. The results are shown in Table 2-3.
(Formulation)
Itraconazole: 20% by mass
Cellulose: 25% by mass
Mannitol: 47% by mass
Macrogol 6000: 5% by mass
Croscarmellose sodium: 2% by mass
Magnesium stearate: 1% by mass

TABLE 2-3

| | Cellulose | Tablet hardness [N] | Disintegration time [min] | Mount — | Elution ratio (60 min) [%] | Elution ratio (120 min) [%] |
|---|---|---|---|---|---|---|
| Ex. 2-1 | A | 64 | 10 | ○ (small mount) | 80 | 84 |
| Ex. 2-2 | B | 70 | 10 | ○ (small mount) | 86 | 91 |
| Ex. 2-3 | C | 50 | 6 | ⊚ (not generated) | 90 | 95 |
| Ex. 2-4 | D | 59 | 6 | ⊚ (not generated) | 92 | 97 |
| Ex. 2-5 | E | 51 | 4 | ⊚ (not generated) | 95 | 100 |
| Ex. 2-6 | F | 52 | 2 | ○ (small mount) | 82 | 86 |
| Ex. 2-7 | G | 51 | 5 | ○ (small mount) | 89 | 94 |
| Com. Ex. 2-1 | H | 110 | 11 | X (generated) | 33 | 35 |
| Com. Ex. 2-2 | I | 30 | 1 | X (generated) | 49 | 52 |
| Com. Ex. 2-3 | J | 117 | 12 | X (generated) | 35 | 37 |
| Ex. 2-8 | A | 53 | 13 | ○ (small mount) | 95 | 100 |
| Com. Ex. 2-4 | I | 25 | 1 | X (generated) | 54 | 63 |
| Ex. 2-9 | E | 70 | 6 | ⊚ (not generated) | 92 | 98 |
| Com. Ex. 2-5 | I | 50 | 2 | X (generated) | 33 | 35 |

As shown in Table 2-3, in the tablets containing cellulose having an alkali-soluble substance in an amount of 32% by mass or more and 44% by mass or less with respect to the total mass of cellulose (Examples 2-1 to 2-7), the disintegration time was short, and the elution rates at 60 minutes and 120 minutes also met the required levels while maintaining good disintegration time and suppressing the generation of mount, as compared with the tablets containing cellulose having an alkali-soluble substance in an amount outside of the above range (Comparative Examples 2-1 to 2-3).

Further, in tablets containing cellulose having an alkali-soluble substance in an amount of 35% by mass or more and 41% by mass or less with respect to the total mass of cellulose (Examples 2-3 to 2-5), the disintegration time was as short as 6 minutes or less, the elution rate at 60 minutes was 90% or more, and the elution rate at 120 minutes was 95% or more, which were particularly excellent.

Further, regarding the tablets in which the content of solubilizer was increased to 20% by mass (Example 2-8 and Comparative Example 2-4), in the tablet containing cellulose A in which the content of the alkali-soluble substance was 32% by mass with respect to the total mass of cellulose (Example 2-8), the disintegration time was short, and the elution rates at 60 minutes and 120 minutes also met the required levels while maintaining good hardness and suppressing the generation of mount, as compared with the tablets containing cellulose I having an alkali-soluble substance in an amount outside of the above range (Comparative Example 2-4).

Further, regarding the tablets (Example 2-9 and Comparative Example 2-5) in which the content of the solubilizer was reduced to 5% by mass, in the tablet containing cellulose E having the alkali-soluble substance in an amount of 41% by mass with respect to the total mass of cellulose (Example 2-9), the disintegration time was short, and the elution rates at 60 minutes and 120 minutes also met the required levels while maintaining good hardness and suppressing the generation of mounts, as compared with the tablet containing cellulose I having an alkali-soluble substance in an amount outside of the above range (Comparative Example 2-5).

Examples 2-10 to 2-16 and Comparative Examples 2-6 to 2-8

Using the celluloses shown in Table 2-4 below, the raw materials of the following formulations were mixed to prepare formulation powders. The formulation powders were then used to prepare tablets (9.5 mmo, 600 mg/tablet) with a rotary tableting machine (tableting pressure: 9 kN). The obtained tablets were evaluated in various ways by the methods described above. The results are shown in Table 2-4.
(Formulation)
Acetazolamide: 42% by mass
Cellulose: 25% by mass
Mannitol: 30% by mass
Cross povidone: 2% by mass
Magnesium stearate: 1% by mass

TABLE 2-4

| | Cellulose | Tablet hardness [N] | Disintegration time [min] | Elution ratio (90 min) [%] |
|---|---|---|---|---|
| Ex. 2-10 | A | 69 | 13 | 76 |
| Ex. 2-11 | B | 75 | 11 | 78 |
| Ex. 2-12 | C | 58 | 8 | 80 |
| Ex. 2-13 | D | 62 | 7 | 82 |
| Ex. 2-14 | E | 55 | 5 | 85 |
| Ex. 2-15 | F | 55 | 6 | 77 |
| Ex. 2-16 | G | 57 | 8 | 80 |

TABLE 2-4-continued

| | Cellulose | Tablet hardness [N] | Disintegration time [min] | Elution ratio (90 min) [%] |
|---|---|---|---|---|
| Com. Ex. 2-6 | H | 112 | 13 | 47 |
| Com. Ex. 2-7 | I | 36 | 1 | 51 |
| Com. Ex. 2-8 | J | 118 | 15 | 49 |

As shown in Table 2-4, in the tablets containing a cellulose having an alkali-soluble substance in an amount of 32% by mass or more and 44% by mass or less with respect to the total mass of cellulose (Examples 2-10 to 2-16), the disintegration time was short, and the elution rate at 90 minutes also met the required level while maintaining good hardness, as compared with the tablets containing a cellulose having an alkali-soluble substance in an amount outside of the above range (Comparative Examples 2-6 to 2-8).

Further, in the tablets containing a cellulose having an alkali-soluble substance in an amount of 35% by mass or more and 41% by mass or less with respect to the total mass of cellulose (Examples 2-12 to 2-14 and 16), the disintegration time was as short as 8 minutes or less, and the elution rate at 90 minutes was 80% or more, which was particularly excellent.

INDUSTRIAL APPLICABILITY

According to the cellulose powder of the present embodiment, it is possible to suppress the generation of mount during the elution test of active ingredient in vitro while maintaining good moldability and disintegration property. The cellulose powder of the present embodiment is suitable for an orally disintegrating tablet (OD tablet). In addition, the tablet of the present embodiment contains a poorly water-soluble medicinal ingredient and has good moldability, disintegration property and elution property.

The invention claimed is:

1. A cellulose powder comprising a cellulose-derived alkali-soluble substance capable of dissolving in 17.5% by mass of aqueous sodium hydroxide solution, the content of the cellulose-derived alkali-soluble substance being 32% by mass or more and 44% by mass or less with respect to the total mass of the cellulose powder, wherein
an aerated bulk density of the cellulose powder is 0.12 g/cc to 0.24 g/cc.

2. The cellulose powder according to claim 1, wherein the cellulose-derived alkali-soluble substance is contained in an amount of 33% by mass or more and 42% by mass or less with respect to the total mass of the cellulose powder.

3. The cellulose powder according to claim 1, wherein the average particle size of primary particles of the cellulose powder is 10 μm or more and 50 μm or less.

4. The cellulose powder according to claim 1, wherein the water absorption amount is 160% or more and 360% or less.

5. The cellulose powder according to claim 1, wherein the ratio (L/D) of the major axis to the minor axis of the cellulose particles is 1.8 or more and 3.5 or less.

6. The cellulose powder according to claim 1, wherein the average particle size is 10 μm or more and 200 μm or less.

7. A method for suppressing mount formation, wherein the cellulose powder defined in claim 1 is used for a preparation to be subjected to a dissolution test of active ingredient.

8. A tablet comprising
at least one active ingredient, and
the cellulose powder defined in claim 1.

9. The tablet according to claim 8, wherein the active ingredient is a poorly water-soluble medicinal ingredient.

10. The tablet according to claim 9, wherein the medicinal ingredient is classified as Class 2 or Class 4 according to the regulations of the biopharmaceutical classification system adopted by the FDA.

11. The tablet according to claim 8, further comprising a solubilizer in an amount of 0.1% by mass or more and 30% by mass or less with respect to the total mass of the tablet.

12. The tablet according to claim 8, wherein the hardness of the tablet is 50 N or more.

13. The tablet according to claim 8, wherein the content of the cellulose is 1% by mass or more and 99% by mass or less with respect to the total mass of the tablet.

14. The tablet according to claim 8, wherein the content of the medicinal ingredient is 0.01% by mass or more and 50% by mass or less with respect to the total mass of the tablet.

* * * * *